United States Patent [19]
Rutherford

[11] Patent Number: 5,150,722
[45] Date of Patent: Sep. 29, 1992

[54] MULTI-LAYER SCENT EMITTING ARTICLE AND DEVICE ADAPTED TO EMPLOY SAME

[75] Inventor: Howard J. Rutherford, Highlands, N.J.

[73] Assignee: International Flavors & Fragrances Inc., New York, N.Y.

[21] Appl. No.: 611,913

[22] Filed: Nov. 9, 1990

Related U.S. Application Data

[63] Continuation-in-part of Ser. No. 407,064, Sep. 14, 1989, Pat. No. 5,069,231, which is a continuation-in-part of Ser. No. 379,175, Jul. 12, 1989.

[51] Int. Cl.$^5$ .................. A24F 47/00; B67D 5/10; B32B 9/04
[52] U.S. Cl. .................. 131/335; 131/270; 131/329; 131/231; 222/3; 222/4; 428/411.1; 428/414; 428/497
[58] Field of Search ............ 131/329, 270, 335, 273, 131/231; 428/411.1, 414, 497; 222/3, 4

[56] References Cited

U.S. PATENT DOCUMENTS

Re. 33,299  8/1990  Sweeny et al.
4,720,417  1/1988  Sweeny et al.
4,988,546  1/1991  Tanner.
4,990,381  2/1991  Holzner.

FOREIGN PATENT DOCUMENTS 8907429  8/1989  PCT Int'l Appl.
2209532  5/1989  United Kingdom.

Primary Examiner—V. Millin
Attorney, Agent, or Firm—Arthur L. Liberman

[57] ABSTRACT

Described are methods for effecting the controlled release of fragrance materials over a relatively long period of time for the purpose of air treatment and scenting. Optionally in the same time frame the methods can effect an initial "Burst" of the same or different organoleptic functional materials over a relatively short period of time. The air treatment agents can include but are not limited to insect repellents, air fresheners, odorants and deodorants. Also described are articles capable of being mass produced which are useful in effecting the controlled release of fragrances, insect repellents, air fresheners, odorants and deodorants over a relatively long period of time and, optionally, in the same time frame, effecting an initial "Burst" of the same or different organoleptic functional materials over a relatively short period of time. Also described is apparatus specifically designed to utilize such articles.

9 Claims, 15 Drawing Sheets

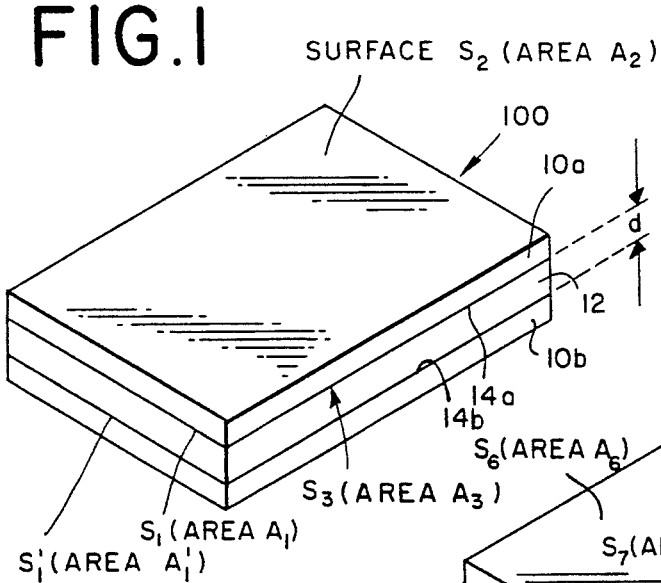
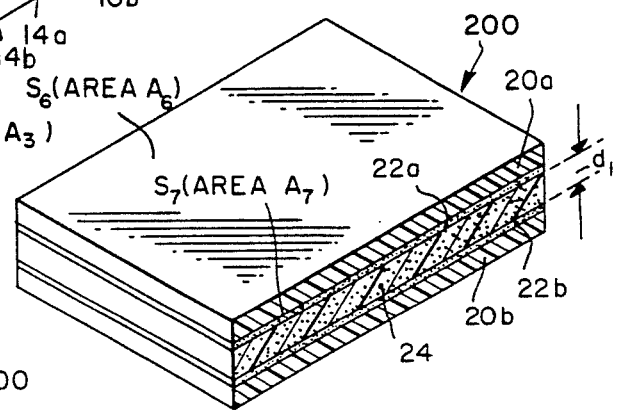
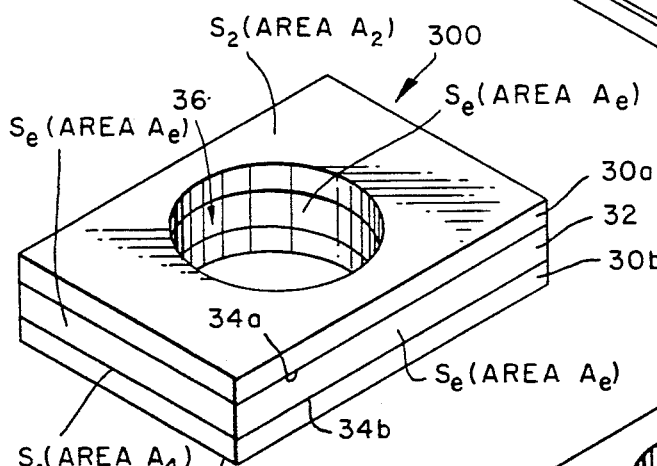
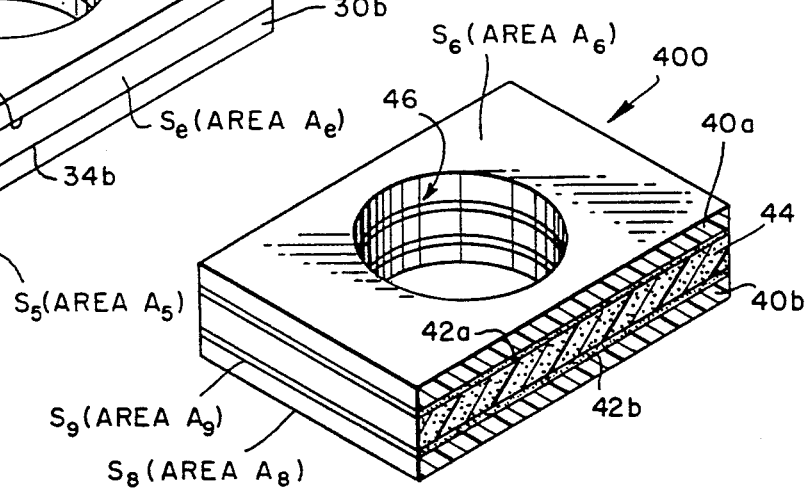

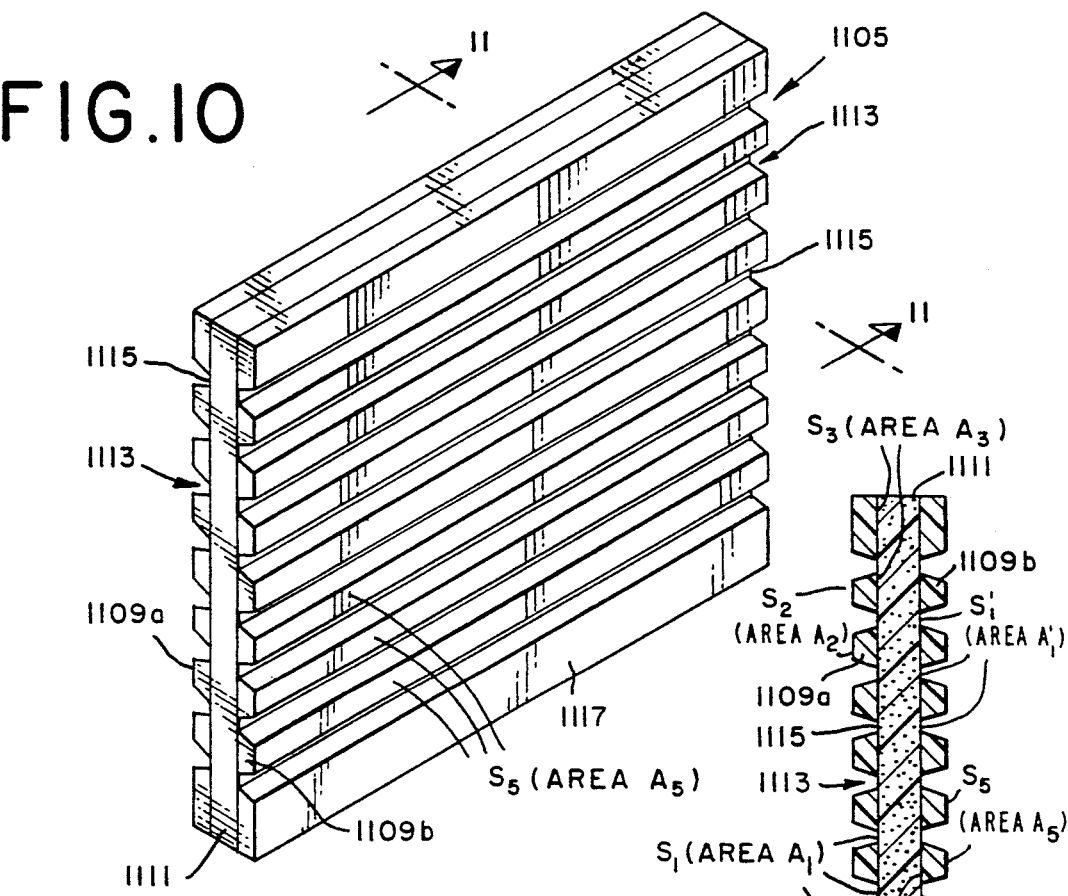
FIG. 10
FIG. 11
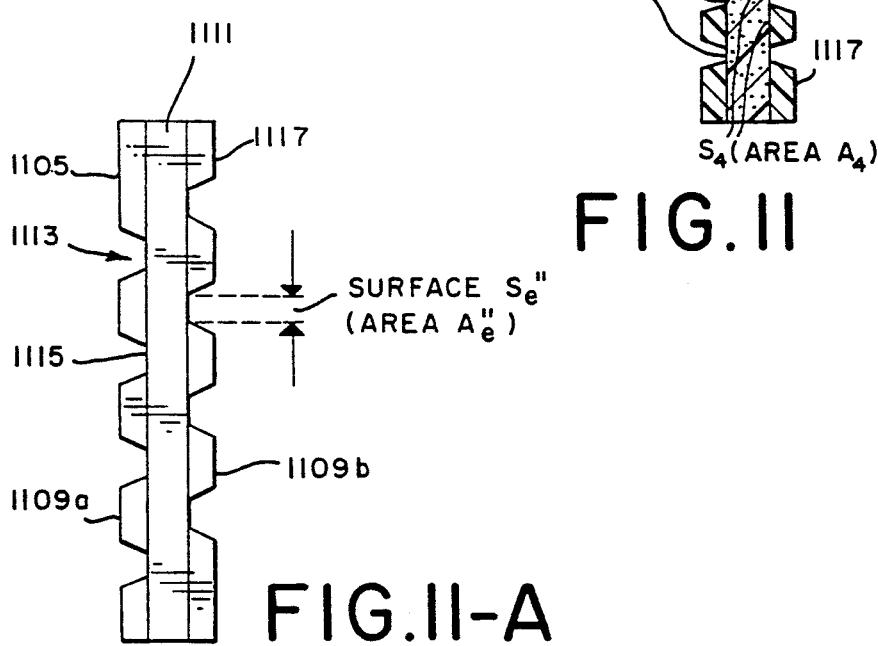
FIG. 11-A

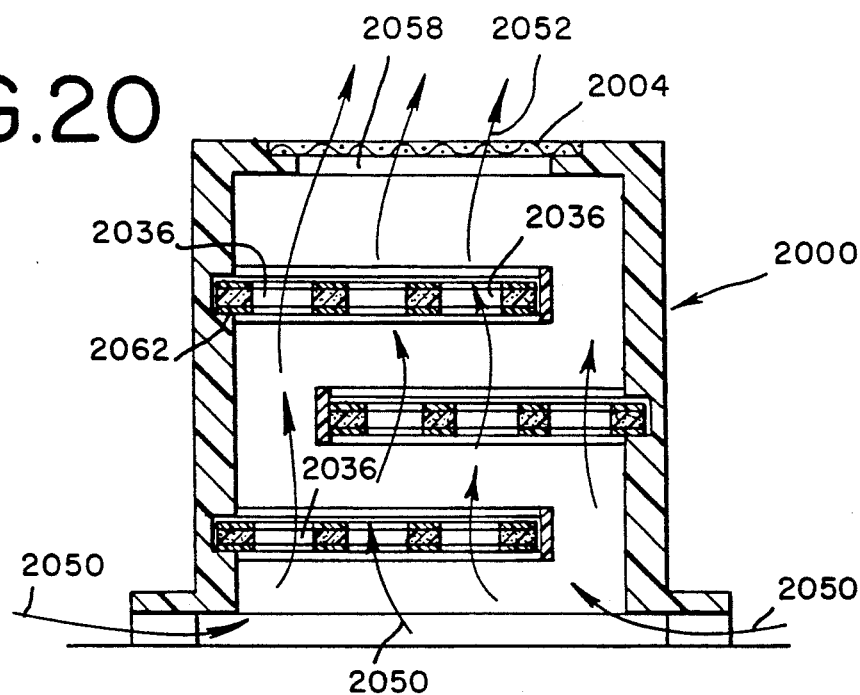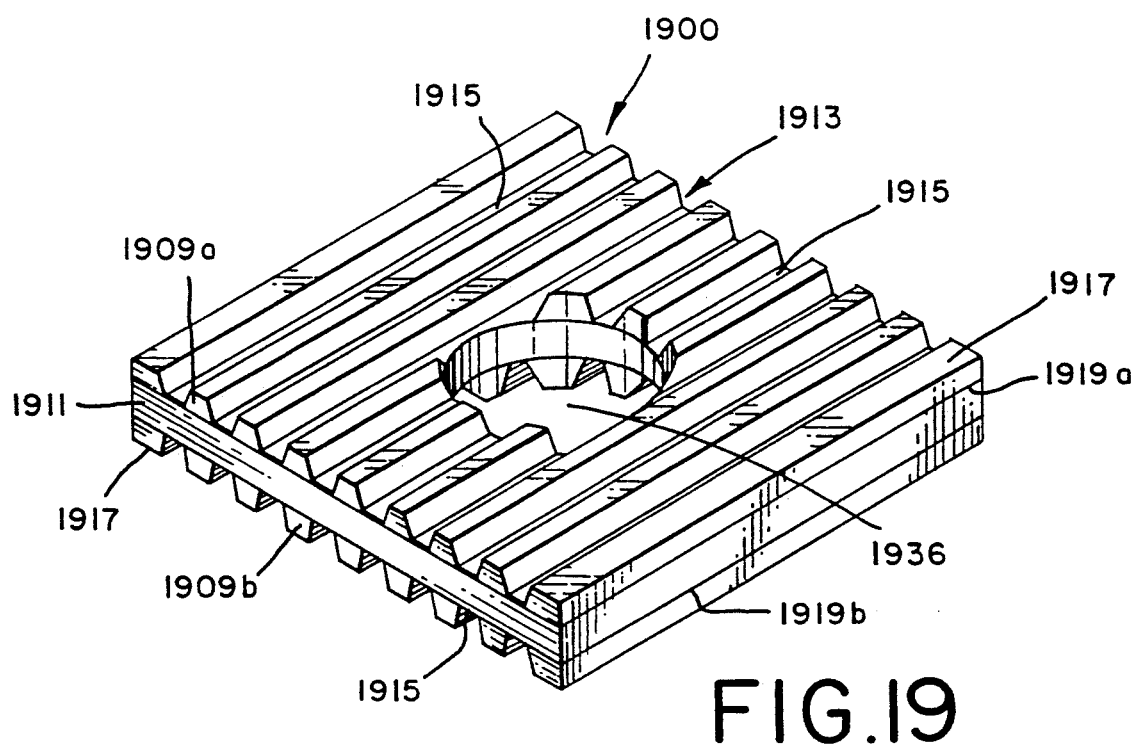

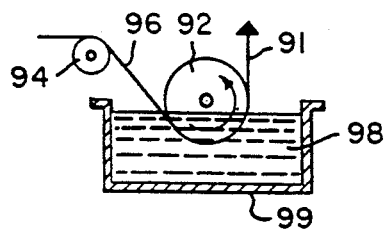
FIG.23
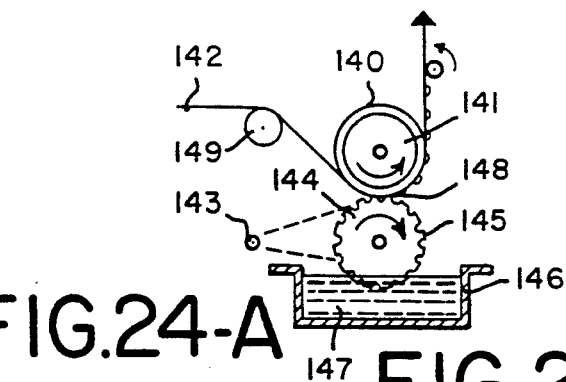
FIG.24-A  FIG.28
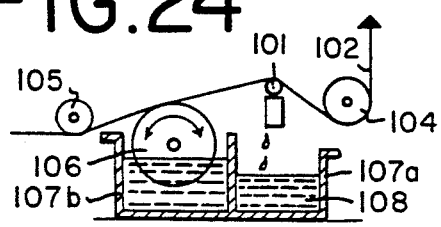
FIG.24
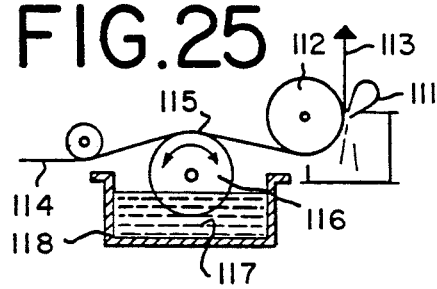
FIG.25
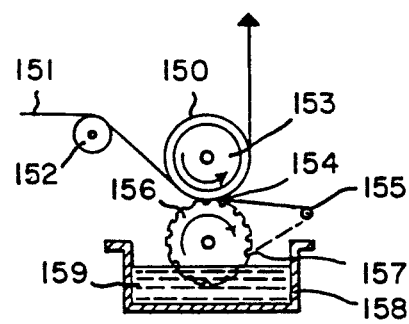
FIG.29
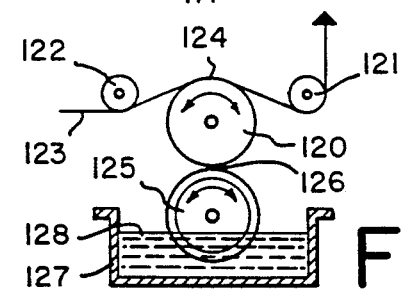
FIG.26
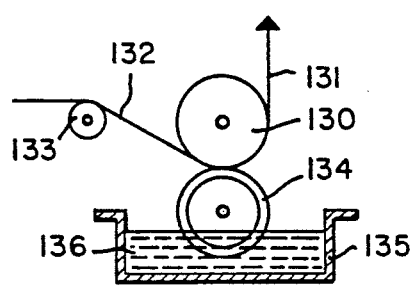
FIG.27
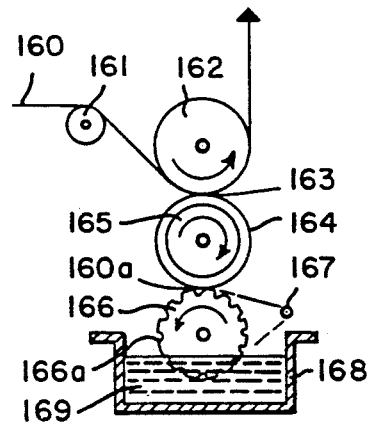
FIG.30

FIG.31
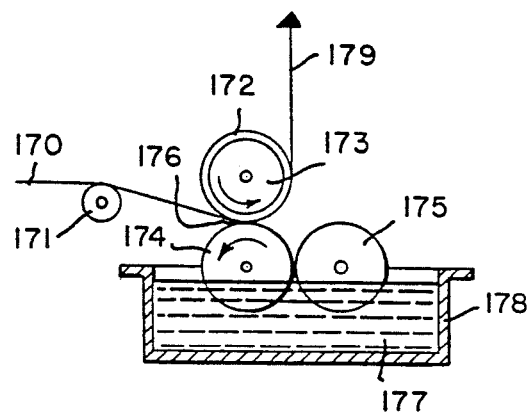
FIG.32
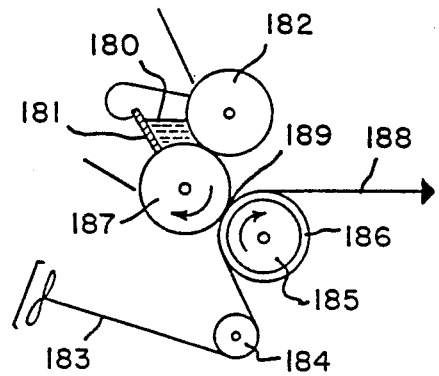
FIG.33-A
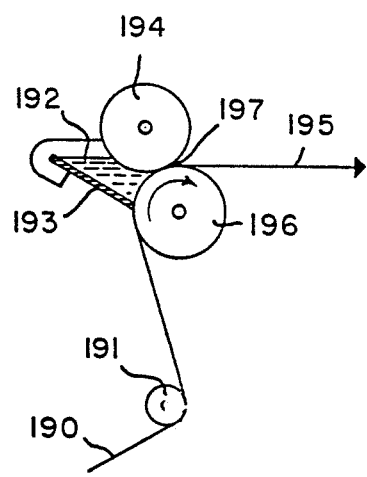
FIG.33-B
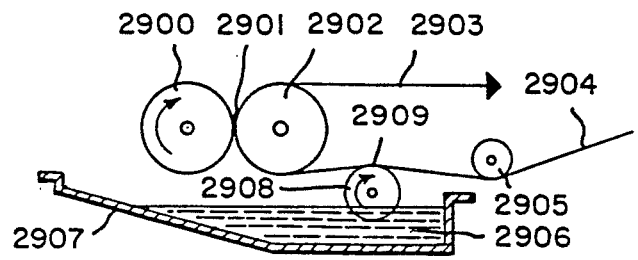

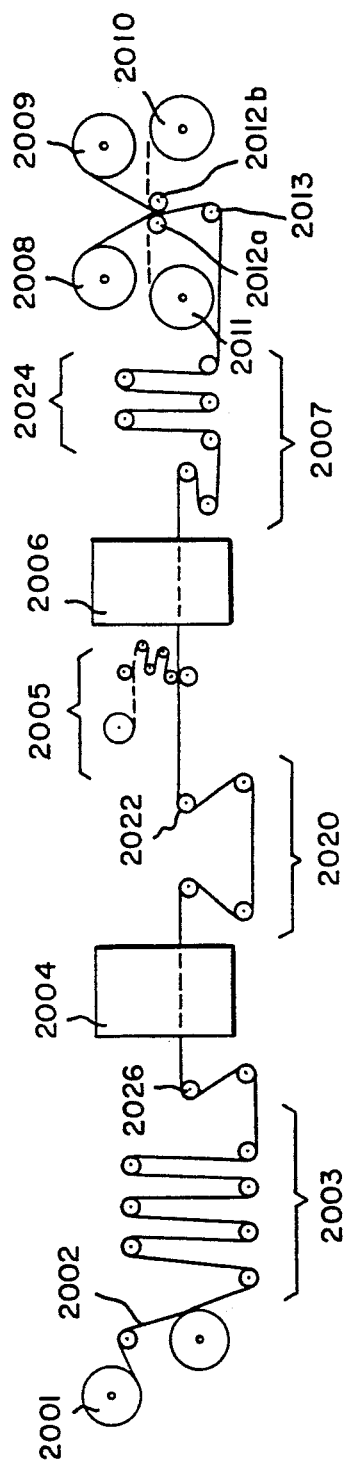
FIG. 34
FIG. 35

FIG.36
FIG.37-A
FIG.37-B
FIG.38
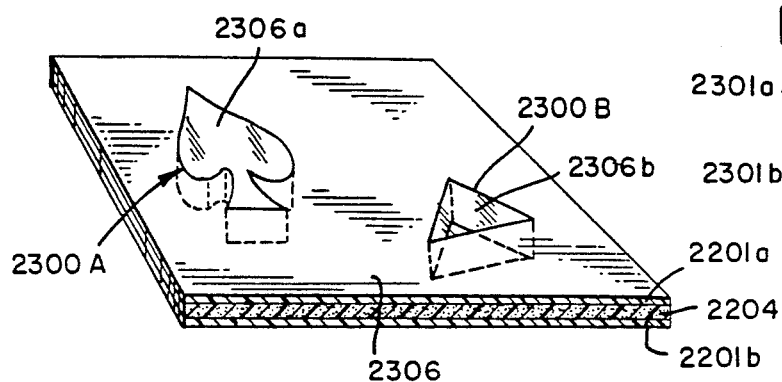
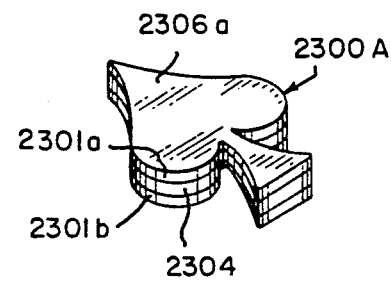
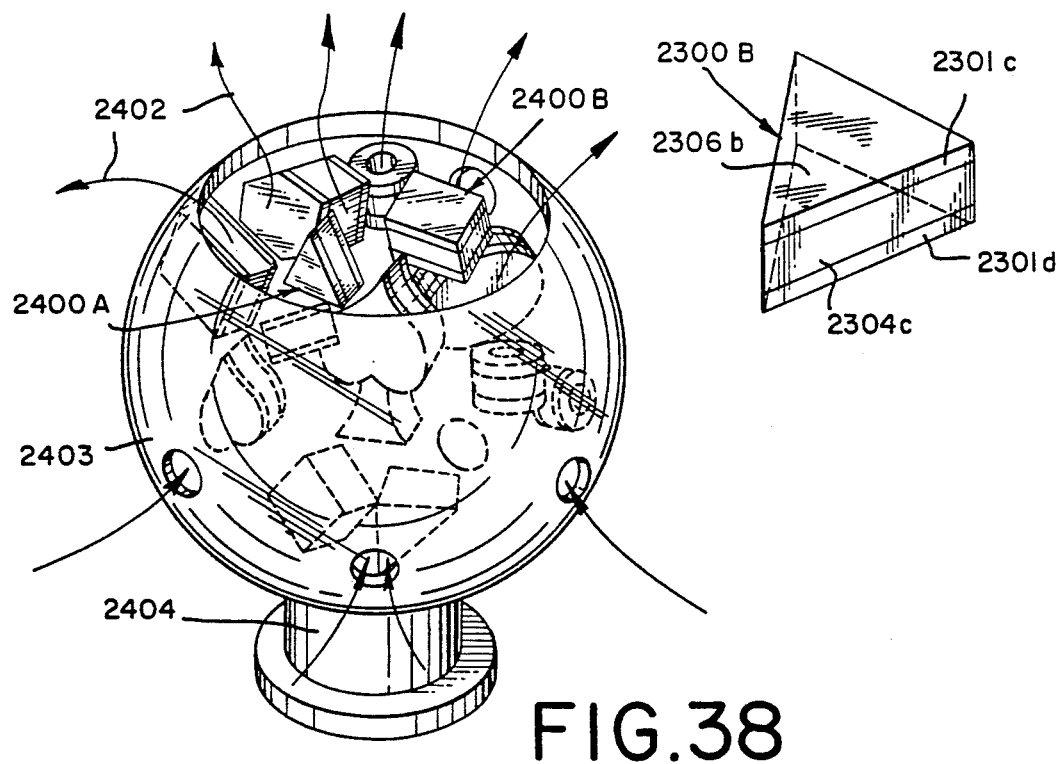

MULTI-LAYER SCENT EMITTING ARTICLE AND DEVICE ADAPTED TO EMPLOY SAME

BACKGROUND OF THE INVENTION

The present invention relates to a multi-layer sustained release scent emitting article having a high effective scent emitting exposure surface area comprising two barrier layers covering the planar surfaces of the functional ingredient-containing material. The present invention also relates to methods for using such an article for effecting the controlled release of insect repellents, air fresheners, odorants and deodorants over a relatively long period of time and, optionally, in the same time frame effecting an initial "Burst" of the same or different functional materials over a relatively short period of time.

Various articles intended to release a fragrance over a long period of time are well known. The fragrances employed include both aromatic and perfumed compositions. An early form of such device, and one still in use, was a pomander made by studding an apple or orange with cloves and useful as a garment sachet. Another approach still in use is to enclose dried leaves or flower petals in a perforated bag, box or other container. More recently, various solid substrates such as waxes or polymeric materials have been impregnated with fragrances for use, for example, as room fresheners. In such applications, a steady and controlled rate of release of the fragrance from the substrate is a desirable attribute. The uses of waxes or polymeric materials as substrates or carriers has the further advantage that the fragrance-containing materials can readily be formed or cut into virtually any desired shape or size.

As specific examples of the known materials described above, U.S. Pat. No. 3,567,119 to Wilburt discloses a method for incorporating fragrance compounds, oil bouquets or other agents into polymeric or natural materials so that the fabricated product possesses the properties imparted by the agent or agents for a long period of time; this method requires the use of surfactants for incorporating the agents and the duration of the agent in the fabricated product is enhanced by employing antioxidants and/or ultraviolet radiation absorbers. U.S. Pat. No. 3,303,046 to Chebiniak, et al describes a composition containing pores which express liquid upon the application of pressure, formed from mixing an aqueous latex of a polymer with a plasticizer and heating to produce an aqueous composition containing dispersed droplets or plasticizer in which a coloring material may be dispersed. U.S. Pat. No. 4,493,869 to Sweeney, et al describes fragrance-releasing appliques that provide a transparent or translucent substrate bearing microcapsules containing the fragrance in a binder on one surface. U.S. Pat. No. 4,254,179 to Carson, et al describes a method and apparatus for impregnating a porous foam product with a fragrance that can be released over an extended period of time. U.S. Pat. No. 4,257,176 to Hartung, et al describes an insole for footwear that has an odor masking or malodor counteractant material dissolved, trapped or encapsulated in a somewhat resilient resin coating through which it will progressively migrate or bleed under application of foot loads, foot perspiration and elevated foot temperatures to the surface of the coating to be released into the footwear to mask or counteract foot odors. U.S. Pat. No. 4,226,944 to Stone, et al discloses fragrance-emitting articles comprising a polyurethane foam containing a particulate filler and a fragrance material and a method of making such an article.

PCT Application 89/07429 published on Aug. 24, 1989 and assigned to Cygnus Research Corporation claims, inter alia, "Discloses a method for making a fragrance-releasing device, comprising:
(a) laminating an adsorbent source layer, adapted to initially retain a fragrance in liquid form, to a pressure-sensitive, pharmaceutically acceptable adhesive carrier which defines a basal surface;
(b) depositing a fragrance in liquid form on one face of the adsorbent source layer, whereby the fragrance is incorporated and initially retained therein;
(c) laminating an anchor adhesive layer to the opposing face of the source layer, the anchor adhesive layer comprised of a material that is substantially permeable to the fragrance; and
(d) applying a backing layer to the anchor adhesive layer which defines the upper surface of the device and is substantially permeable to the fragrance."

PCT Application 89/07429 further describes a device for the controlled release of fragrance into the atmosphere comprising:

"(a) a backing layer that is substantially permeable to the fragrance and which defines the upper surface of the device;
(b) an anchor adhesive layer adjacent the backing layer and laminated thereto, wherein the anchor adhesive layer is comprised of a material that is substantially permeable to the fragrance;
(c) a layer of a pressure-sensitive, pharmaceutically acceptable contact adhesive layer which defines the basal surface of the device; and
(d) an adsorbent fibrous source layer in contact with and contained between layers (b) and (c) and into whose void volume at least a portion of layers (a) and (b) has flowed; and
(e) a fragrance dissolved in layer (b), said portion of layer (b) and optionally layer (c) and said portion of layer (c)."

Published United Kingdom Patent Application 2,209,532A published on May 17, 1989 (Applicant: Thermedics Inc.) having a priority in the United States of Sep. 9, 1987, U.S. application Ser. No. 095,055, discloses a fragrance-emitting article or perfume patch which comprises a polyurethane having a perfume dispersed therein wherein in one embodiment of the article there is included a fragrance-emitting member having a fragrance dispersed within the polyurethane layer. A layer of pressure-sensitive adhesive is applied to the article so that it may be adhered to a surface. The polyurethane is formed from a diisocyanate, a macroglycol, and an acrylyl chain terminator to which a photoinitiator and a fragrance oil are added prior to photo-curing. A barrier or support layer is applied by an adhesive or other suitable means to prevent migration of the fragrance oil to the adhesive layer so that no residue of adhesive remains on the surface.

None of the articles of the prior art concern the type of article of the instant invention wherein two barrier layers surround the two exposed surface of a functional ingredient, emitting laminar where the functional ingredient is emitted in a controlled release manner through a "gate" from the edges of the article and/or from defined discreet relatively small surface area sections of the article.

BRIEF DESCRIPTION OF THE DRAWINGS

FIG. 1 is a perspective view of a first embodiment of an article of my invention containing a control release element but not containing any "Burst" layers.

FIG. 2 is a second embodiment of the article of my invention containing a sandwiched control release layer adhered via the adhesive layers to two barrier layers but not containing a "Burst" layer.

FIG. 3 is a perspective view of a third embodiment of the article of my invention particularly designed for use in potpourris or air freshener sachets; but no "Burst" layer is contained thereon.

FIG. 4 is a perspective view of a fourth embodiment of the article of my invention showing a sandwiched control release scenting layer surrounded by barrier layers; but not including any "Burst" layer.

FIG. 10 is a perspective view of another embodiment of the article of my invention useful for air fresheners.

FIG. 11 is a cut-away side elevation view of the article of FIG. 10 taken along lines 11—11 of FIG. 10.

FIG. 11A is a cut-away side elevation view of an article which is a variation of the article of FIG. 10 adapted for use with air freshener apparatus.

FIG. 17 shows the preloading of said articles and FIG. 18 shows the apparatus with the articles loaded and ready to use.

FIG. 19 is a perspective view of another embodiment of the articles of my invention utilizable in the operation of the apparatus of FIG. 5 as well as the apparatus of, inter alia, FIG. 16.

FIG. 20 is a cut-away side elevation view of another embodiment of the air freshener apparatus of my invention utilizing articles of, for example, FIG. 19.

FIG. 23 is a schematic diagram of "Roll coating" apparatus of the "Dip" type useful in producing such articles as illustrated in FIG. 1.

FIG. 24 is a schematic cut-away side elevation view of "Roll coating" apparatus of the "Mayer rod" type useful in producing such articles as that illustrated in FIG. 1.

FIG. 25 is a schematic diagram of a cut-away side elevation of "Roll coating" apparatus of the "Air Knife" type.

FIG. 26 is a schematic diagram of a cut-away side elevation view of "Roll coating" apparatus of the "Kiss" type useful in fabricating articles of my invention as illustrated in FIG. 1.

FIG. 27 is a schematic diagram of a cut-away side elevation view of "Roll coating" apparatus of the "Squeeze roll" type useful in fabricating articles of my invention of the type illustrated in FIG. 1.

FIG. 28 is a schematic diagram of a cut-away side elevation view of "Roll coating" apparatus of the "Gravure" type useful in fabricating articles of my invention of the type illustrated in FIG. 1.

FIG. 29 is a schematic diagram of a cut-away side elevation view of "Roll coating" apparatus of the "Reverse gravure" type useful in fabricating articles of my invention as illustrated in FIG. 1.

FIG. 30 is a schematic diagram of a cut-away side elevation view of "Roll coating" apparatus of the "Offset gravure" type useful in fabricating articles of my invention of the type illustrated in FIG. 1.

FIG. 31 is a schematic diagram of a cut-away side elevation view of "Roll coating" apparatus of the "Reverse roll" type useful in fabricating articles of my invention as illustrated in FIG. 1.

FIG. 32 is a schematic diagram of a cut-away side elevation view of "Roll coating" apparatus of the "Nip-reverse roll" type useful in fabricating articles of my invention of the type illustrated in FIG. 1.

FIG. 33A and FIG. 33B sets forth, respectively, the applicator roll section and the backing roll section of "Roll coating" apparatus of the "Levelon" type useful in fabricating articles of my invention of the type illustrated in FIG. 1.

FIG. 34 is a schematic cut-away side elevation view of "Transfer coating" apparatus for a polyurethane transfer coating line apparatus useful in fabricating articles of my invention of the type illustrated in FIG. 1.

FIG. 35 is a schematic cut-away side elevation view of another embodiment of the "Transfer coating" apparatus; which is a PVC transfer coating line with convection ovens useful in fabricating articles of my invention of the type illustrated in FIG. 1.

FIG. 36 is a perspective view of another embodiment of the articles of my invention showing the use of such articles in creating articles having an ornamental design for the purpose of being used as air freshening articles, perfuming articles and insect repellents articles of my invention.

FIG. 37A and FIG. 37B are perspective views of articles having an ornamental design created as a result of cutting such articles from the article of FIG. 36.

FIG. 38 is a perspective view of a transparent container containing a synthetically produced "potpourri" prepared by admixing such articles as illustrated in FIGS. 37A and 37B and placing them in a container which is transparent.

SUMMARY OF THE INVENTION

Figure 5:
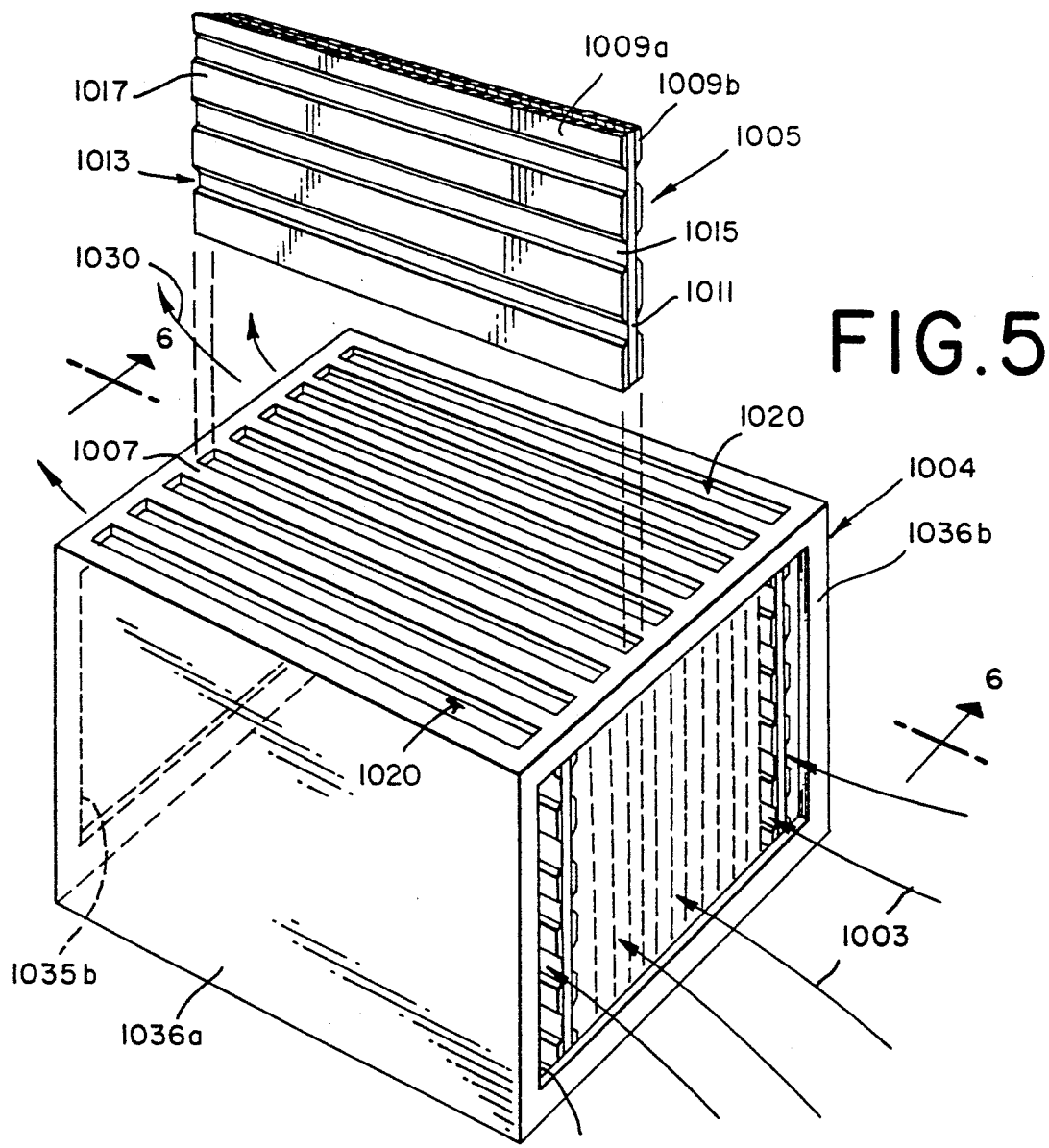
FIG. 5 is a perspective view in schematic form illustrating an air freshener or environmental treatment apparatus containing articles of my invention; and showing one of the articles removed from the apparatus for illustration purposes.

The invention concerns methods for effecting the controlled release of functional organoleptic materials, to wit:

(i) Fragrances;
(ii) Tobacco flavors;
(iii) Air fresheners;
(iv) Deodorants; and
(v) Insect repellents over a relatively long period of time using specially fabricated laminar articles. Optionally, in the same time frame, an initial "Burst" of the same or different organoleptic functional materials can be effected over a relatively short period of time.

This invention also relates to laminar articles, capable of being mass produced, which are useful in effecting the controlled release of functional organoleptic materials, to wit:

(i) Fragrances;
(ii) Tobacco flavors;
(iii) Air fresheners;
(v) Deodorants;
(vi) Insect repellents;

over a relatively long period of time. Optionally, the articles can include a feature that gives rise to an initial "Burst" of the same or different organoleptic functional materials over a relatively short period of time. This invention also covers apparatus, optionally, computer program-controlled, for fabricating the aforedescribed articles.

More specifically, my invention relates to a multi-layer sustained release tobacco flavor, scent, insect repellent, deodorant and/or air freshener emitting laminar article comprising:

(a) a sustained release agent, tobacco flavor insect repellent, deodorant and/or air freshener-emitting substantially planar core lamina consisting of a microporous of macroporous polymer having included in the pores thereof a fragrance, tobacco flavor, insect repellent, deodorant and/or air freshener composition, said core lamina having a first upper planar surface $S_1$ of surface area $A_1$, a second lower planar surface $S_1'$ of surface area $A_1'$, a substantially uniform finite cross section thickness $d_1$ and a lateral continuous or discretely interrupted surface area $S_e$ having an area $A_e$ (which surface area is exposed to the environment surrounding the article) being substantially in linear lateral core planes immediately adjacent to, or conterminous to and juxtaposed to one another or in a curvilinear lateral core plane or in curvilinear lateral core planes immediately adjacent to or conterminous to and juxtaposed to one another, said lateral core plane or core planes being substantially perpendicular to said first upper planar surface and said second lower planar surface on said core lamina; wherein:

$$S_e \perp (S_1 \wedge S_1')$$

and $$A_1 = A_1' >> A_e;$$

(b) fixedly adhered to said first upper planar surface of said core lamina and contiguous (or coplanar) therewith at least one planar impermeable polymeric first barrier lamina or series of spaced monoplanar spaced parallel first barrier laminae which has a first upper surface, $S_2$ of surface area $A_2$ and a second lower surface, $S_3$ of surface area $A_3$, said second lower surface being fixedly contiguous (or coplanar) with said first upper planar surface of said core lamina with the provisos that:

$$A_1 = A_1' \geq A_3 \geq A_2$$

and $$S_1 \parallel S_1', \parallel S_3 \parallel S_2$$

(c) fixedly adhered to said second lower planar surface $S_1'$ of said core lamina and contiguous (or coplanar) therewith at least one planar impermeable polymeric second barrier lamina or series of spaced parallel second barrier laminae which has a first upper surface $S_4$ of surface area $A_4$ and a second lower surface $S_5$ of surface area $A_5$, said first upper surface $S_4$ being fixedly contiguous (or coplanar) with said second lower planar surface $S_1'$ of the core lamina with the provisos that:

$$A_1' \geq A_4 \geq A_5$$

and $$S_1' \parallel S_4 \parallel S_5;$$

optionally:

(d) fixedly adhered to said first upper surface $S_2$ of said first barrier lamina and contiguous (or coplanar) therewith a porous or microporous "Burst" immediate release scent, tobacco flavor, insect repellent, deodorant and/or air freshener-emitting substantially planar first "Burst" lamina or series of monoplanar spaced parallel first "Burst" laminae consisting of a microporous or macroporous polymer having included in the pores thereof a fragrance, tobacco flavor, insect repellent, deodorant and/or air freshener composition, said first "Burst" lamina having a first upper outer exposed surface (that is, exposed to the environment surrounding the article) $S_6$ of surface area $A_6$ and a second lower inner surface $S_7$ of surface area $A_7$, said surface $S_7$ being fixedly contiguous (or coplanar) with said first upper surface $S_2$ of said first barrier lamina with the provisos that:

$A_2 \geqq A_7$ and $S_2 \| S_7$;

optionally:

(e) fixedly adhered to said second lower surface $S_5$ of said second barrier lamina and contiguous (or coplanar) therewith a porous or microporous scent, tobacco flavor, insect repellent, deodorant and/or air freshener-emitting substantially planar second "Burst" lamina or series of monoplanar spaced parallel second "Burst" laminae consisting of a microporous or macroporous polymer having included in the pores thereof a fragrance, tobacco flavor, insect repellent, deodorant and/or air freshener composition, said second "Burst" lamina having a first lower outer exposed surface (that is, exposed to the environment surrounding the article) $S_8$ of surface area $A_8$ and a second upper inner surface $S_9$ of surface area $A_9$, said surface $S_9$ being fixedly contiguous (or coplanar) with said surface $S_5$ with the provisos that:

$A_5 \geqq A_9$ and $S_5 \| S_9$

The method of this invention, for example, permits obtaining (i) a long lasting spearmint-fresh aftertaste when a cigarette is smoked after having been kept on the shelf for a year or longer and (ii) a short term high intensity "Burst" of spearmint aftertaste immediately on the smoking of the cigarette. Similarly, it provides laminar air freshener articles in which the release of the aroma-imparting composition can be controlled as to rate, intensity and length of use.

In another aspect of the invention, the article can be comprised of (1) a core polymer (2) a first covering polymer and (3) a second covering polymer, which have differing rates of water solubility, so that the first covering, the second covering and the core will dissolve at different rates and provide for release of functional material, which in this embodiment could also include such materials as fabric softeners, surfactants, anti-static agents, and the like. It will be apparent from the present disclosure that the articles can be used for a wide variety of products. Thus one or more of such articles can be incorporated into filters such as those for use in cigarettes. The articles of the present invention can also be used in air fresheners and the like. The present invention thus provides methods for modifying the organoleptic properties of a wide variety of products, as will be appreciated by those skilled in the art from the present disclosure.

Figure 39:
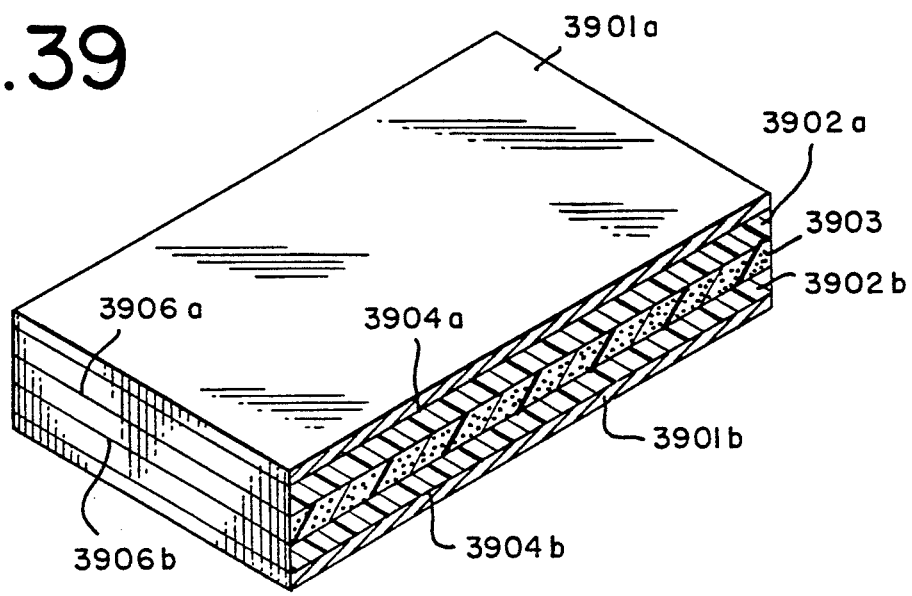
FIG. 39 is perspective view of another embodiment of the article of my invention showing a central control release layer surrounded by impermeable barriers with the impermeable barriers each covered by "Burst" layers for immediate release of such materials as insect repellents, air fresheners and perfume.

Thus the present invention simultaneously can provide (i) controlled delivery systems and (ii) initial impact high intensity delivery systems in the same article for delivery of organoleptic functional materials or compositions for a variety of uses. In cigarette filter articles, the systems deliver flavor where the "gate" or area through which the controlled release flavor is delivered as disclosed hereinafter is the open end of the laminar article. The "Burst" flavor is simultaneously delivered (as shown in FIG. 39). In a controlled delivery-initial impact high intensity delivery system for air fresheners, the gate is the exposed section of the core polymer usually but not always the open cut ends of the laminar article. For controlled delivery-initial impact high intensity delivery in a laundry system, a water-soluble material leaches out from the core polymer while, for example, perfumery material exits from the outer functional material "Burst" coating, and further control can also be obtained by the use of various polymers on the exterior. In this case, a barrier coating of polypropylene is more hydrophilic than low-density polyethylene or polyethylene-vinyl acetate and a functional ingredient "Burst" coating of polyethylene-vinyl acetate is more hydrophilic than high density polyethylene.

The present invention can also be applied to make soluble materials with a water-insoluble barrier film 3902a and 3902b (when referring to FIG. 39), thin with respect to the interior core 3903 and the exterior water soluble coatings 3901a and 3901b. In the case of these water-soluble products, fabric softeners, detergents, bleaches, and other materials such as described in U.S. Pat. No. 4,842,761 could be placed in the interior of the article for release by leaching.

The present invention also contemplates methods for the production of such controlled release/initial "Burst" flavoring and fragrance articles which methods comprise introducing the polymer and the flavoring material, separately or together, into extrudate means to form a mixture of the polymer and flavoring composition, drawing the mixture through orifice means to form a generally laminar extrudate and simultaneously with the drawing of the mixture covering the laminar extrudate with (1) a barrier material and (2) an initial "Burst" material to form two outer coatings covering and contiguous with the extrudate to provide the final laminar article. The extrudate is subsequently cooled in a liquid, and is supplied to the user, e.g., a cigarette or cigarette filter manufacturer in the form of a sheet of the laminar material. Alternatively, as disclosed hereinafter the articles can be furnished in the form of cut up sheets ready for incorporation or use in a product.

The user can then cut the laminar sheets into individual articles for incorporation into the ultimate product which it is desired to flavor, or fragrance. In the case of filter cigarettes, the flavor-modifying articles of this invention can be supplied by cutting the laminar sheets into smaller articles with high-speed machinery and continuously supplying the laminar smaller articles to filter materials to incorporate the laminar articles into filter cigarettes. It will be appreciated by those skilled in the art from the present description that the flavor-containing article can also be provided directly in the form of small laminar articles by cutting the extrudate immediately instead of providing it in large sheet form. The present invention thus also provides methods for altering or enhancing or improving the flavors of consumable materials. In other embodiments of the invention, a laminar product can be provided in generally larger sizes for incorporation, e.g., into air freshener products and insect repellent products. The size of the laminar article is selected as appropriate for the flavor or fragrance or insect repellent or deodorant or air freshener released. In other embodiments, the laminar articles can be prepared to have the first polymer and second polymer with different solubilities in a selected medium, such as water, so that they can be used in laundering compositions.

The polymer core component and the flavor and/or aroma and/or insect repellent and/or air freshener "Burst" component of the organoleptic articles of this invention are in general normally solid polymers. The polymer can be the same or different water soluble polymers in certain aspects of the invention disclosed herein, but it is preferable in certian desired embodiments of the invention that they be water-insoluble. The polymers are chosen so that they are compatible with the organoleptic compositions used and so that they are each materials which do not contain and will not produce during use toxic materials or products. The core polymer as well as the functional ingredient "Burst" polymer used to carry the organoleptic functional compositions are relatively more permeable to the constituents of the organoleptic functional composition than the second or barrier polymer and should also be stable to the conditions of use. Thus, if they are to be used in a cigarette filter, they should be capable of withstanding the temperatures, gases and vapors occasioned by the passage of the combustion products through the filter. For air freshener uses, the core polymer or polymers and the functional "Burst" polymer or polymers (when employed) should of course be capable of withstanding the conditions of storage and use, that is, among other factors the temperatures and humidities to be encountered.

It will be understood that the filter in which the flavoring articles of this invention are used can be comprised of any materials used in cagarette filters. Filters most usually contain compacted cellulosic material which is produced in several ways. However, such filters can also include other or entirely different components which absorb or adsorb components of the main smoke stream. Sometimes the filters also contain components which will absorb or otherwise capture one or more undersired components of the smoke stream. In any event, the laminar flavoring articles of the present invention are readily used with all such filter materials.

The normally solid core polymers as well as the functional ingredient "Burst" polymers for use herein can incorporate mixtures of various polymers, depending upon the properties desired. Thus, when multiple cores are used in the articles of this invention, the several cores can be comprised of the same or different polymers and these core polymers may be the same as or different from the functional ingredient "Burst" polymers (when such "Burst" polymers are indeed used). Among the water-insoluble polymers used herein for the core material as well as the functional ingredient "Burst" polymers are low-density polyethylene, high-density polyethylene, copolymers of ethylene and vinyl acetate, polypropylene, polyvinyl chloride, cellulose acetate, methyl cellulose, cellulose acetate-butyrate, polyisobutylene, and the like. Mixtures of 50-70 parts of low-density polyethylene and 30 to 10 parts of polyethylene-vinyl acetate, (copolymers) have been found to provide good results, and such mixtures are preferred in certain embodiments of the invention.

An additional property required of (a) the polymer core material and (b) the functional ingredient "Burst" polymer material (when used) in the production of cigarette filters is stiffness, so that the coated extrudate can readily be cut by the high-speed machinery used in the manufacture of the cigarette. If the core material or the functional ingredient "Burst" polymer material are each too stiff, they will cause the cutter blades to wear rapidly and necessitate frequent shutdowns of the machinery to permit blade changes. If the core material and/or the functional ingredient "Burst" polymer material are too soft, they will not cut cleanly.

As taught above, the organoleptic material-bearing core is surrounded (i) by a layer of second material which substantially bars passage of the organoleptic material from the core which may, in turn, be surrounded if desired (as shown in FIG. 39); (ii) by a functional ingredient "Burst" polymer layer. In other words, the permeability of the second material with respect to the organoleptic functional composition is substantially less than that of the core material and substantially less than that of the functional ingredient "Burst" polymer material (when used). Generally, then, these second polymer barrier materials in desired embodiments of the invention are to be selected to be less pervious to the organoleptic compositions and to provide the properties required in the product.

In general, the barrier materials are crystalline polymers. Examples of barrier materials which be used are polyamides, polyesters, polyvinyl derivatives such as polyvinyl chloride, polyolefins containing three or more carbon atoms, such as polypropylene, polybutylene and the like, polyepoxides such as crystalline homopolymers of ethylene oxide or polymers of bisphenol-A with epichlorohydrin, and block polymers such as copolymers of propylene and polyethylene of the polyalymer type, and the like. The polyamides are highly crystalline and are preferred in certain embodiments of the invention.

As stated, supra, the functional ingredient "Burst" polymer coating on the barrier material includes polymers similar in permeability characteristics to the core polymers. The preferred polymer is polyethylene-vinyl acetate.

It will be understood according to the present invention that there is considerable latitude in formulating laminar articles according to the present invention. When the articles are to be used for inclusion in cigarette filters, there is a need to maintain a relatively small size and properties which fit the articles for high-speed production. For cigarette filter laminar flavoring articles, they must adequately deliver the flavor immediately over the time that the cigarette is being smoked. For air fresheners, only a small quantity of material may need be released over a relatively short period of time, but there should be long-term release of the organoleptic substance. On the other hand, laminar articles for air freshener uses do not have the same size restrictions in all embodiments, so they can be larger such is also the case when using insect repellents and deodorants. Moreover, the air freshener is expected to deliver a larger quantity of total fragrance material over a longer period of time. The articles of the present invention used in air fresheners may be formulated to yield an initial "Burst" of air freshener or perfuming material and, in addition, flatten the release rate so that the organoleptic composition is released over a longer term in a "controlled release" manner. The present invention accordingly provides means for controlling the release of the flavor and/or aroma composition contained in the core and at the same time effects an initial flavor or aroma "Burst" which is desired and/or required by the ultimate consumer for a wide variety of uses.

If desired, the barrier coating may actually comprise two or more individual coatings designed to exploit the properties of two or more different materials. Thus, if a good barrier material is not satisfactorily adhesive to the core material, an additional intermediate adhesive coating can be used to adhere the barrier coating to the core. By the same token if a functional ingredient "Burst" polymer material is not satisfactorily adherent to the barrier layer, an additional intermediate adhesive coating can be used to adhere the functional ingredient "Burst" polymer coating to the barrier coating. The coatings can also contain a layer serving to improve the processability of the extrudate of organoleptic composition-bearing extrudate. Such adjuvant materials for the barrier layer include lubricants for the cutter blades of the machinery, or surface rougheners so that the cut laminar articles would not stick or jam in the high-speed cigarette processing equipment, such as that mentioned above. Similarly, such additional coatings, processability improvers, intermediate coatings, rougheners, lubricants, and other processing adjuvants can be used to produce laminar products for air fresheners, laundry compositions, and the like.

The barrier coating thickness and the functional ingredient "Burst" polymer coating thickness can each be varied on the outer surface of the lamina article of my invention.

The barrier coating thickness will vary depending upon the insect repellent or organoleptic composition, the particular polymer or other materials (e.g., inorganic mineral materials like calcium carbonate) used in the coating, the ratio of length to diameter of the lamina article, the particular use to which the articles are to be put, and the like.

The functional ingredient "Burst" polymer coating thickness will vary depending upon the length of time that the lamina article is intended to be stored prior to use and the time that it is desired to have the initial high-intensity "Burst" of functional ingredient last. It will thus be appreciated from the present description that it is possible to vary the thickness or presence of the barrier coating. Thus, if the barrier coating were not completely continuous along the surface of the core polymer, the organoleptic composition and/or insect repellent composition release properties can be varied to provide the desired functional activity. Thus, comminuted calcium carbonate or other materials can be incorporated in the coating. This has the effect of opening an additional "gate" for the system. Furthermore, the barrier polymer coating can be in the form of repeated parallel strips such as that set forth in FIGS. 7, 10, 12 and 13 described in detail infra.

One of the important aspects of the present invention is utilized for the preparation of the organoleptically functional articles and methods is the ratio of flat laminar area ($S_i$) to area of core polymer exposed to the environment surrounding the article ($S_e$). This ratio hereinafter defined as "gate ratio", is shown thusly:

$$G.R. = \left[ \frac{(A_i)}{(A_e)} \right]$$

$A_i$ stands for the outer surface area of a single surface of the article and wherein $A_e$ stands for the lateral exposed surface area or total exposed surface area of the core polymer of the article; and wherein G.R. stands for the term "gate ratio".

The laminae of my invention are generally flat in shape; but may be circular, rectangular, square, triangular or in the shape of any polygon of "n" sides (wherein "n" is greater than or equal to 3).

The gate ratio or "G.R." can be readily used to control the quantity and rate of release of the functional material, e.g., fragrance, air freshener, deodorant, tobacco flavor or insect repellent. In effect, there is a "gate" which is controlled by selecting the ratio of one of the exposed upper surface areas of the laminar article of my invention to the exposed surface area of the core containing the functional materials. The exposed core surface area, $A_e$ of the lamina is important because this is the area through which the vast majority of functional organoleptic composition or insect repellent composition will be controllably released (over a relatively long period of time) from the core during use. The lamina surface area of the article will also determine the volume of core and thus to some extent the quantity of functional organoleptic composition which the lamina article will carry which is intended for controlled release of the functional material over a relatively long period of time.

When the laminae of the present invention are used in cigarette filters, it has been found that the gate ratio ("G.R.") is readily adjusted to control the controlled release of the flavor and/or aroma composition from the core. There is a marked variation of release of the flavor or aroma composition from the core when there is no barrier coating on the material. It is generally found that the curve of the weight lost per weight of sample is very steep for the core without barrier coating (as it is for the functional ingredient "Burst" polymer layer). By contrast, when the size of the gate ratio (as defined supra) is increased, the curve of weight lost per weight of sample becomes increasingly flat, particularly after the functional ingredient from the functional ingredient "Burst" polymer layer (when employed) is expended.

The size of the article can also be adjusted and controlled to provide the requisite storage retention and the desired controlled release delivery of the organoleptic composition (from the core) during smoking in the cigarette. Thus, the overall thickness, $d_1$ can be adjusted from as little as 0.05 inches to about 0.3 inches. For an air freshener product the overall size is generally larger than 0.1 inches. In certain desirable air freshener embodiments, the size can range up to one inch and may be varied, depending upon the design and apparatus in which it is utilized, for example, as shown in FIG. 5. In any case the gate ratio (G.R.) can range from about ¼ (0.25) up to about 1/35 (about 0.03). A "G.R." of greater than ¼ (0.25) can be used in some emodiments, but it is generally found that controlled release of the active ingredient or ingredients of the flavor or fragrance or insect repellent composition is too slow (after the functional ingredient from the functional ingredient "Burst" polymer layer (when used is expended). A "G.R." smaller than 1/35 (about 0.03) generally results in the controlled release loss of flavor or aroma composition or insect repellent composition from the core which is too rapid and which is too steep a curve.

It is accordingly desirable that the "G.R." be from about 0.25 to about 0.03. In certain preferred embodiments of the invention, the gate is from about 0.2 up to about 0.04.

In certain preferred embodiments, the laminar article has a substantially circular core parallel to the coatings of the barrier polymer (and optionally parallel to the plane of the functional ingredient "Burst" polymer coating). With such a geometry the gate ratio is shown by the following formula:

$$G.R. = \frac{R}{2d}$$

wherein R is the radius of the circle and d is the thickness of the core lamina.

By the same token, when the geometry gives rise to an article which is a square, the formula for the gate ratio is thus:

$$G.R. = \frac{P}{16d}$$

wherein P is the parameter of the square and d is the thickness of the laminar article.

When the geometry of the article of my invention is such that it is an equilateral triangle the formula for the gate ratio is as follows:

$$G.R. = \frac{1}{4\sqrt{3}} \left( \frac{L}{d} \right)$$

wherein L is the length of a side of the equilateral triangle and d represents the thickness of the core lamina.

Figure 14:
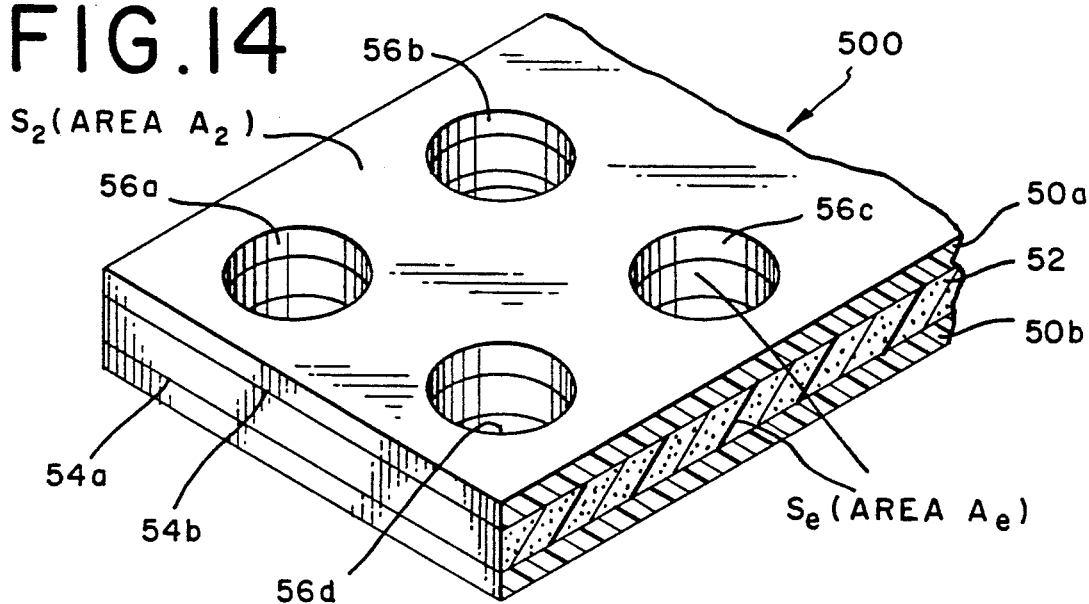
FIG. 14 is a perspective view of another embodiment of the article of my invention wherein the control release scenting layer is sandwiched between two barrier layers and the article has specifically designed holes to permit a greater gate area for release of the scenting material from the scenting layer.
Figure 15:
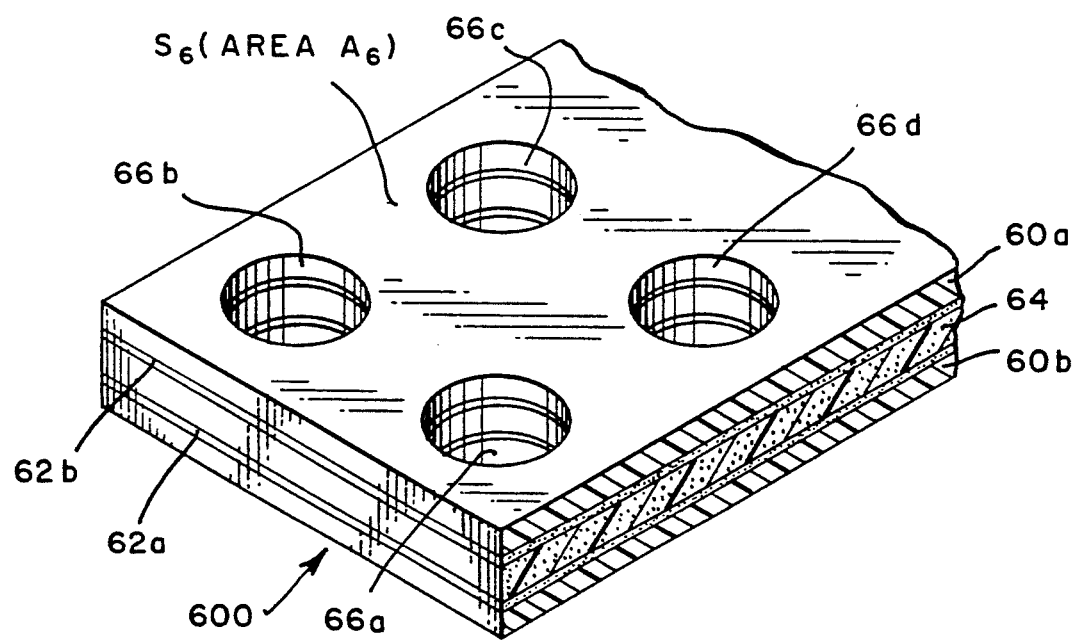
FIG. 15 is a perspective view of another emobidment of the article of my invention containing the scenting layer sandwiched between two barrier layers; without a "Burst" coating and containing holes to permit additional area of scenting layer to be exposed to the environment being treated.

When the geometry of the lamina article of my invention is such that it is a rectangle, the formula for the gate ratio is as follows:

$$G.R. = \frac{LW}{2Ld + 2Wd}$$

where L is the length of the rectangle and W is the width of the rectangle and d is the thickness of the core lamina.

Where the geometry of the laminar article of my invention is in the shape of a rectangle containing a circular void therein as is the case with the structure portrayed in FIG. 3 or the article of FIG. 4) then the formula for the gate ratio is as follows:

$$G.R. = \frac{LW - \pi R^2}{(2L + 2W)d - 2\pi Rd}$$

wherein L is the length of the rectangle; W is the width of the rectangle; R is the radius of the circular void and d is the thickness of the core lamina.

Where the geometry of the article of my invention is such that the lamina article is a rectangle having several circular voids, then as illustrated in FIGS. 14 and 15, then the formula for the gate ratio thereof is as follows:

$$G.R. = \frac{LW - q\pi R^2}{(2L + 2W)d + 2q\pi Rd}$$

wherein L represents the length of the rectangle; W represents the width of the rectangle; R represents the radius of each of the circular voids of the articles; d represents the thickness of the core lamina and q represents the number of circular voids in the article employed.

When the article of my invention has a geometry such that the core lamina is in the form of a rectangle and coated thereon are parallel strips of barrier polymer on each surface of said core lamina, then the formula for the gate ratio for such an article of such a geometric representation is as follows:

$$G.R. = \frac{LW - nLX}{2Ld + 2Wd + nLX + mLX}$$

wherein L is the length of the rectangle core lamina, W represents the width of the rectangular core lamina; d represents the thickness of the core lamina; x represents the width of the core surface between the parallel strips of barrier polymer; n represents the number of parallel barrier polymers strips located on the first suface of the core polymer; and m represents the number of parallel barrier polymer strips on the second surface of the core lamina. Such an article is illustrated in FIG. 10 and is particularly adapted for use in the air freshener apparatus of my invention of FIG. 5.

DETAILED DESCRIPTION OF THE DRAWINGS

Referring to FIG. 1, FIG. 1 is a multi-layer sustained release tobacco flavor, scent, insect repellent, dedorant and/or air freshener-emitting rectangular shaped article $$A_1 = A_1' > > > A_e$$

consisting of:

(a) a sustained release scent, tobacco flavor, insect repellent, deodorant and/or air freshener-emitting substantially planar core lamina 12 consisting of a microporous or macroporous polymer having included in the pores thereof a fragrance, insect repellent, tobacco flavor, deodorant and/or air freshener composition (e.g., a porous vinyl halide-acrylated caprolactone such as that specifically disclosed in U.S. Pat. No. 4,950,693 issued on Aug. 21, 1990 or a polyurethane disclosed in U.S. Pat. Nos. 4,950,694 or 4,950,542 issued on Aug. 21, 1990, the specification for which is incorporated by reference herein), said core lamina having a first upper planar surface $S_1$ of surface area $A_1$, a second lower planner surface $S_1'$ of surface area $A_1'$, a finite cross section thickness $d_1$ and a lateral exposed continuous or discretely interrupted surface area $S_e$ within an area $A_e$ being sustantially in four linear lateral core planes immediately adjacent and perpendicular to one another, said lateral core planes being substantially perpendicular to said first upper planar surface and said second lower planar surface of said core lamina;

(b) fixedly adhered to said first upper planar surface of said core lamina 12 a planar impermeable polymeric first barrier lamina 10a which has a first upper surface of surface area $A_2$ and a second lower surface of surface area $A_3$ said second lower surface being fixedly contiguous with said first upper planar surface of said core lamina 12 at location 14a;

(c) fixedly adhered to said second lower planar surface $S_1'$ of said core lamina 12, a planar impermeable polymeric second barrier lamina 10b which has a third upper surface $S_4$ of surface area $A_4$ and a fourth lower surface $S_5$ of surface $A_5$, said third upper surface $S_4$ being fixedly contiguous with said second lower planar surface $S_1'$ at location 14c.

FIG. 2 illustrates a second embodiment of the article of my invention. Referring to FIG. 2, FIG. 2 is a multi-layer sustained release tobacco flavor, scent, insect repellent, deodorant and/or air freshener-emitting rectangular shaped article 200 consisting of:

(a) a sustained release scent, tobacco flavor, insect repellent, deodorant and/or air freshener-emitting substantially planar core lamina 24 consisting of a microporous or macroporous polymer having included in the pores thereof a fragrance, insect repellent, tobacco flavor, deodorant and/or air freshener composition (e.g., a porous vinyl halide-acrylated caprolactone such as that specifically disclosed in U.S. Pat. No. 4,950,693 issued on Aug. 21, 1990, the specification for which are incorporated by reference herein or a polyurethane disclosed in U.S. Pat. Nos. 4,950,694 or 4,950,542 issued on Aug. 21, 1990, the specifications for which are incorporated by reference herein), said core lamina 24 having a first upper planar surface $S_1$ of surface area $A_1$ having an adhesive layer 22a coated thereon, a second lower planar surface $S_1'$ of surface $A_1'$ having an adhesive layer 22b coated thereon, a finite cross section thickness $d_1$ in a lateral exposed discretely interrupted surface area $S_e$ having an area $A_e$ being substantially in four linear lateral core planes immediately adjacent and perpendicular to one another, said lateral core planes being substantially perpendicular to said first upper planar surface and said second lower planar surface of said core lamina 24;

(b) fixedly adhered via adhesive layer 22a to said first upper planar surface of said core lamina 24a planar impermeable polymeric first barrier lamina 20a which has a first upper surface of surface area $A_2$ and a second lower surface of surface area $A_3$, said second lower surface being fixedly contiguous with the adhesive layer 22a covering said first upper planar surface of said core lamina 24;

(c) fixedly adhered via adhesive layer 22b to said second lower planar surface $S_1'$ of said core lamina 24, a planar impermeable polymeric second barrier lamina 20b which has a third upper surface $S_4$ of surface area $A_4$ and a fourth lower surface $S_5$ of surface $A_5$, surface $S_5$ (being exposed to the environment surrounding the article), said third upper surface $S_4$ being fixedly contiguous (via adhesive layer 22b) with said second lower planar surface $S_1'$.

FIG. 3 illustrates a third embodiment of the article of my invention wherein a circular void, 36, perpendicular to the upper and lower laminar surfaces of the article and transverse from the upper laminar surface to the lower laminar surface of the aritcle.

Figure 16:
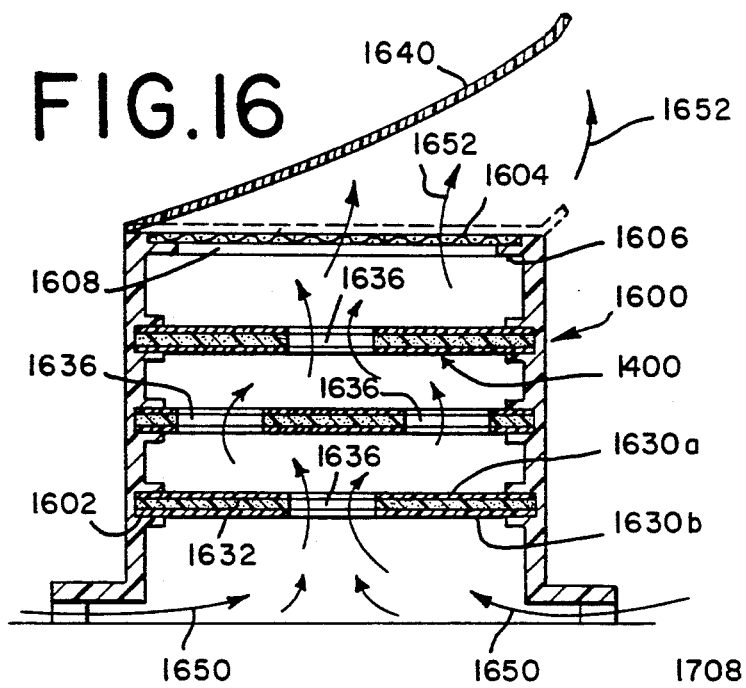
FIG. 16 is a cut-away side elevation view of another embodiment of air freshener apparatus of my invention utilizing the articles of my invention as illustrated, inter alia, in FIG. 14.

Thus, referring to FIG. 3, FIG. 3 is a multi-layer sustained release tobacco flavor, scent, insect repellent, deodorant and/or air freshener-emitting rectangular-shaped article 300 having a circular void therethrough, 36, consisting of:

(a) a sustained release scent, tobacco flavor, insect repellent, deodorant and/or air freshener-emitting substantially planar core lamina 32, consisting of a microporous or macroporous polymer having included in the pores thereof a fragrance, insect repellent, tobacco flavor, deodorant and/or air freshener composition, said core lamina 32 having a first upper planar surface $S_1$ of surface area $A_1$, a second lower planar surface $S_1'$ $A_1'$, a finite cross section thickness $d_1$ and two lateral exposed surface areas; one continuous and one discretely interrupted, $S_e$ having an area $A_e$; the first exposed area being substantially in four linear lateral core planes immediately adjacent and perpendicular to one another, the second exposed area being a circular lateral core plane, part of the circular void 36; said lateral core plane or core planes being substantially perpendicular to said first upper planar surface and said second lower planar surface of said core lamina 32;

(b) fixedly adhered to said first upper planar surface of said core lamina 32, a planar impermeable polymeric first barrier lamina 30a which has a first upper surface of surface area $A_2$ (exposed to the environment surrounding the article) and a second lower surface area $A_3$, said second lower surface being fixedly contiguous with said first upper planar surface of said core lamina 32 at location 34a;

(c) fixedly adhered to said second lower planar surface $S_1'$ of said core lamina 32 a planar impermeable polymer second barrier lamina 30b which has a third upper surface $S_4$ of surface area $A_4$ and a fourth lower surface $S_5$ of surface $A_5$ (said surface $S_5$ being exposed to the environment surrounding the article) said third upper surface $S_4$ being fixedly contiguous with said second lower planar surface $S_1'$ at location 34b. The presence of the circular void 36 permits use of such articles as the one illustrated for air freshener apparatus as illustrated in FIG. 16. Such articles also produced by means of cutting from a much larger sheet (reference is made to FIG. 36) are useful in a potpourri as illustrated in FIG. 38.

FIG. 4 illustrates a fourth embodiment of the article of my invention similar to that of FIG. 3 with the exception that an adhesive layer (42a or 42b adheres to the upper impermeable barrier lamina 40a and the lower impermeable barrier lamina 40b to the central core lamina 44). The article also has a central circular void 46 situated in a direction perpendicular to the outer laminar surface of the upper impermeable polymeric lamina 40a and the lower surface of the lower impermeable polymeric lamina 40b. The said fourth embodiment is referred to by reference numeral 400.

FIGS. 5, 6, 7, 8, 9, 10, 11, 11A, 12 and 13 all concern articles specially adapted for air freshener, deodorant or insect repellent use. Apparatus using such articles (illustrated in FIGS. 5, 6, 8 and 9) requires specially-adapted articles. Specially designed articles employed in the apparatus set forth in FIGS. 5, 6, 8, and 9 are illustrated in FIGS. 7, 10, 11, 11A, 12 and 13.

The specially adapted articles will be described first; followed by a description of the apparatus using said articles.

Figure 7:
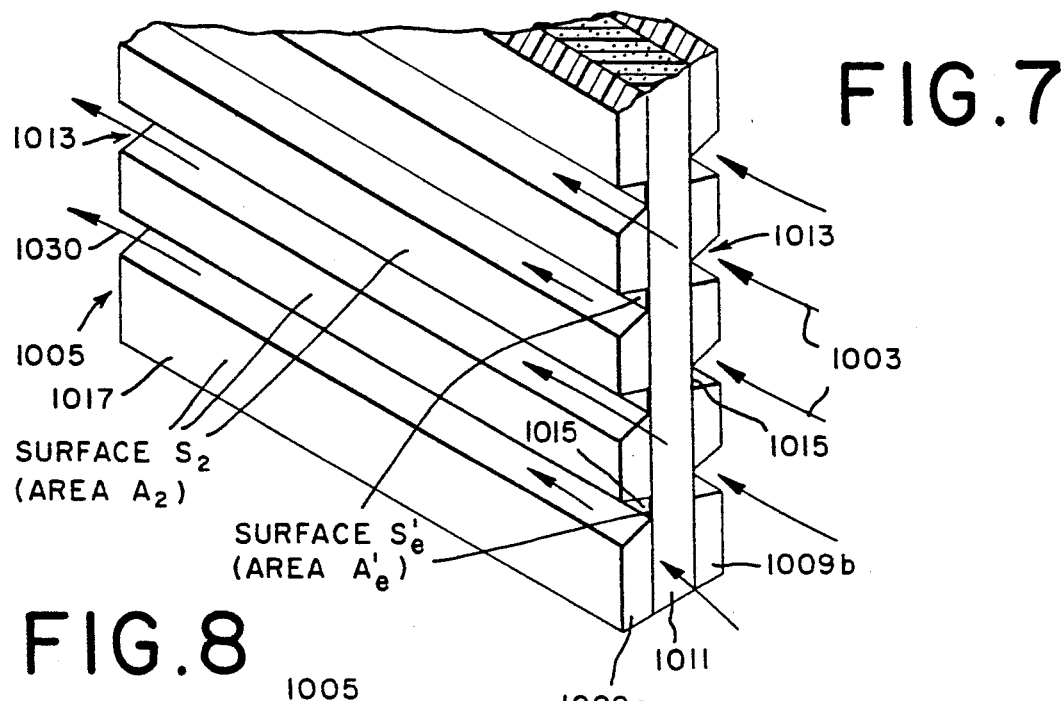
FIG. 7 is a perspective view of a fifth embodiment of the article of my invention specifically designed to be used with the apparatus of FIGS. 5 and 6.

Referring to the article set forth in perspective in FIG. 7, FIG. 7 is a multi-layer sustained release insect repellent, deodorant, and/or air freshener-emitting rectangular-shaped article. Article 1005 consisting of:

(a) a sustained release insect repellent, deodorant, and/or air freshener-emitting substantially planar core lamina 1011 consisting of a microporous polymer having included in the pores thereof an insect repellent, deodorant and/or air freshener composition, said core lamina 1011 having a first upper planar surface $S_1$ of surface area $A_1$ having separately spaced n parallel exposed rectangular areas $A_e''$ thereon 1015, a second lower planar surface $S_1'$ of surface area $A_1'$ having m separately spaced parallel exposed rectangular areas thereon, 1015, a finite cross thickness section $d_1$ and a lateral exposed discretely interrupted surface area $S_e'$ having an area $A_e'$ being substantially in linear lateral core planes immediately adjacent and perpendicular to one another, said lateral core planes being substantially perpendicular to said first upper planar surface and said second lower planar surface of said core lamina 1011;

(b) fixedly adhered to said first upper planar surface of said core lamina 1011, a series of spaced parallel-disposed planes monoplanar first barrier laminae 1009a which have first upper surfaces 1017 of surface area $A_2$ and second lower surfaces of surface area $A_3$, said second lower surfaces each being fixedly contiguous with said first upper planar surface of said core lamina; with the spaces between the parallel-disposed barrier laminae being indicated by reference numeral 1013; and the surface area of said spaces 1013 ($S_e''$) along surface $S_1$ being indicated by reference numeral 1015; (wherein)

$$A_e = A_e' + A_e''$$

(c) fixedly adhered to said second lower planar surface $S_1'$ of said core lamina 1011, a parallel-disposed series of m spaced second barrier laminae 1009b which have third upper surfaces $S_4$ of surface area $A_4$ and fourth lower surfaces $S_5$ of surface area $A_5$, said third upper surfaces $S_4$ being fixedly contiguous with said second lower planar surface $S_1''$.

The articles illustrated in FIGS. 10, 11, 11A, 12 and 13 are similar in structure to the article illustrated in FIG. 7. The articles of FIGS. 10 and 11 are intended to show a larger number of parallel-disposed spaced barrier laminae 1113 having outer surface areas 111 and spaced such that the outer upper and lower exposed surfaces of core lamina 1111 are indicated by reference numeral 1115. The elements per se are indicated by reference numeral 1105. FIG. 10 is a perspective view of the article and FIG. 11 is a cut-away side elevation view along lines 11—11 of FIG. 10.

In FIG. 11A the parallel-disposed series of spaced barrier laminae on the core lamina are less numerous than those of the articles of FIG. 7 or FIG. 10.

Figure 12:
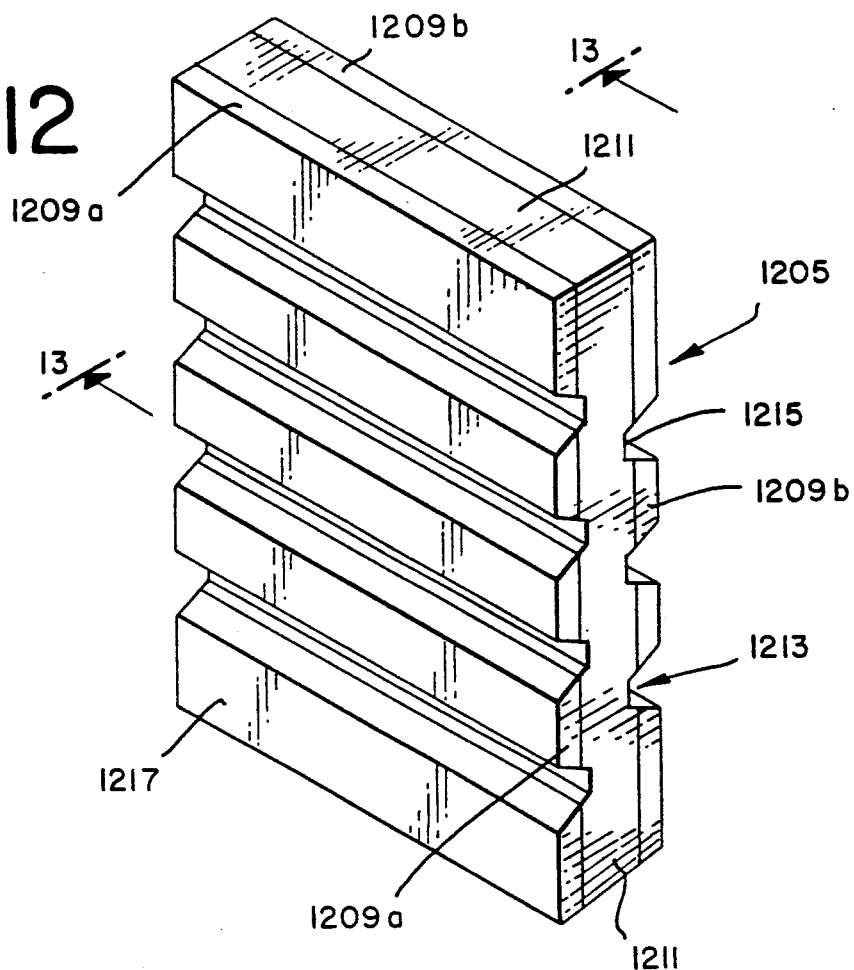
FIG. 12 is a perspective view of another embodiment of the article of apparatus specifically adapted for use with air freshener apparatus.
Figure 13:
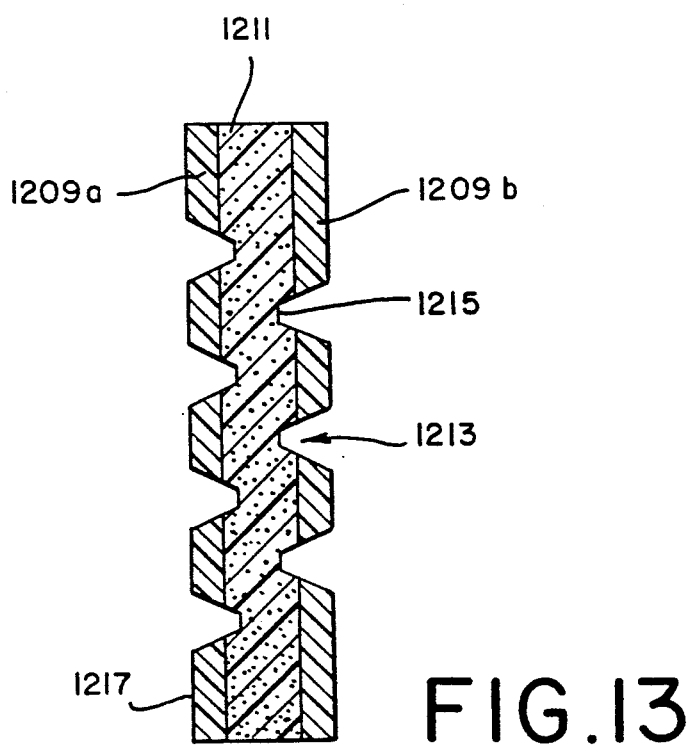
FIG. 13 is a cut-away side elevation view of the article of FIG. 12 taken along 13—13 of FIG. 12.

The articles of FIGS. 12 and 13 are similar to the articles of FIGS. 7, 10, 11 and 11A except that the depth of the ridges 1213 between the parallel-disposed series of spaced barrier laminae 1209a is set well into the core lamina 1211 with the bottom portion of the space between the parallel-disposed series of spaced barrier laminae 1209a being indicated by reference numeral 1215 and with the surface of each of the parallel-disposed series of spaced barrier laminae being indicated by reference numeral 1217.

FIG. 12 is a perspective view of the article and FIG. 13 is a cut-away side elevation view of the same article along lines 13—13 of FIG. 12.

The article of FIG. 7 is shown in perspective view used in an air freshener apparatus in FIG. 5. Thus FIG. 5 shows the article of FIG. 7 inserted into the container 1004 having side walls 1035b and 1036b which have openings whereby air is taken in at 1003 passed the articles 1005. Reference numeral 1011 is the core lamina of article 1005; reference numerals 1009a, 1009b, 1013, 1015 and 1017 are described supra. Article 1005 is inserted into slot 1007 of the box 1004 with a clearance between slot 1007 and article 1005 shown by reference numeral 1020.

Air to be treated is taken in at 1003 and treated air is shown at exhaust 1030 after the air has been in contact with the exposed core polymer at 1015, the core polymer lamina being indicated by reference numeral 1011. The air passes through the notches 1013 and clearance 1020.

Figure 8:
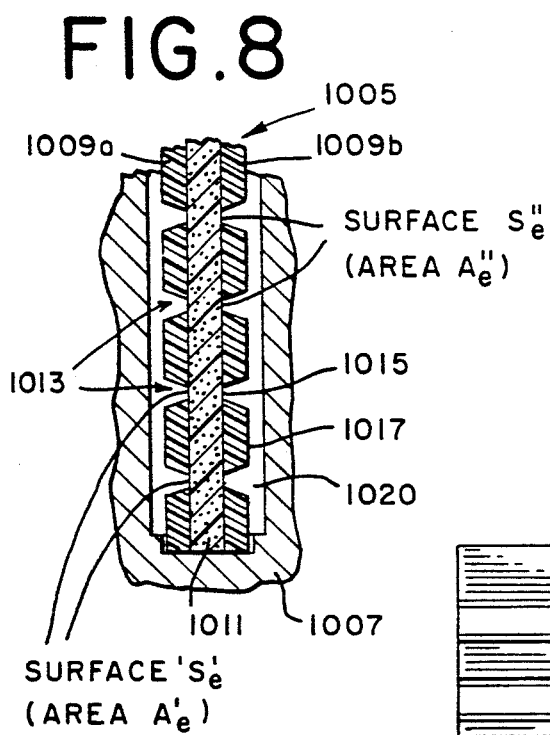
FIG. 8 is a cut-away side elevation view of the article of FIG. 7 along lines 8—8 of FIG. 7.

FIG. 8 is a cut-away side elevation view of a detailed section of article 1005 in place in the apparatus of FIG. 5 with the clearance between article 1005 and the side wall 1007 being indicated by reference numeral 1020.

Figure 9:
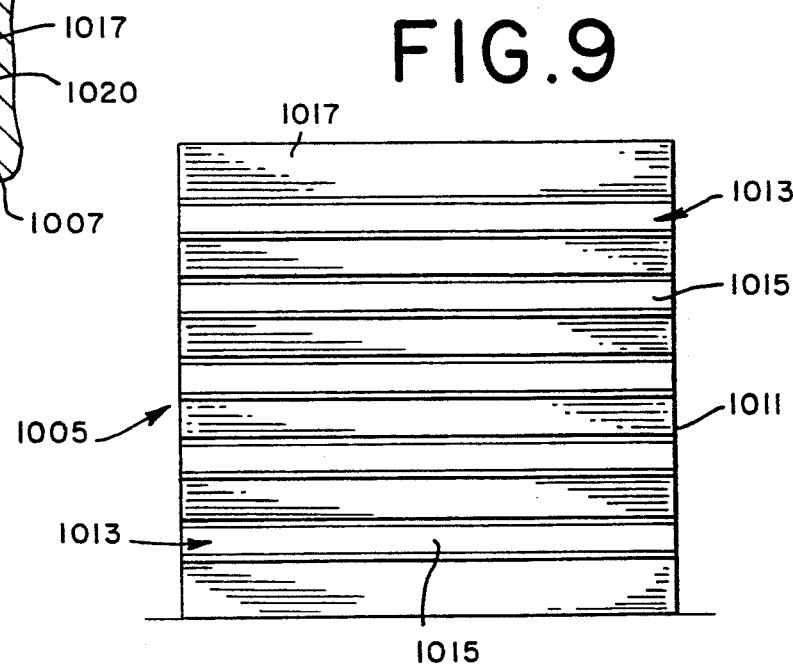
FIG. 9 is a top view of the article of FIG. 7.

FIG. 9 is a top view of the apparatus of FIG. 5 with the articles 1005 in place.

Figure 6:
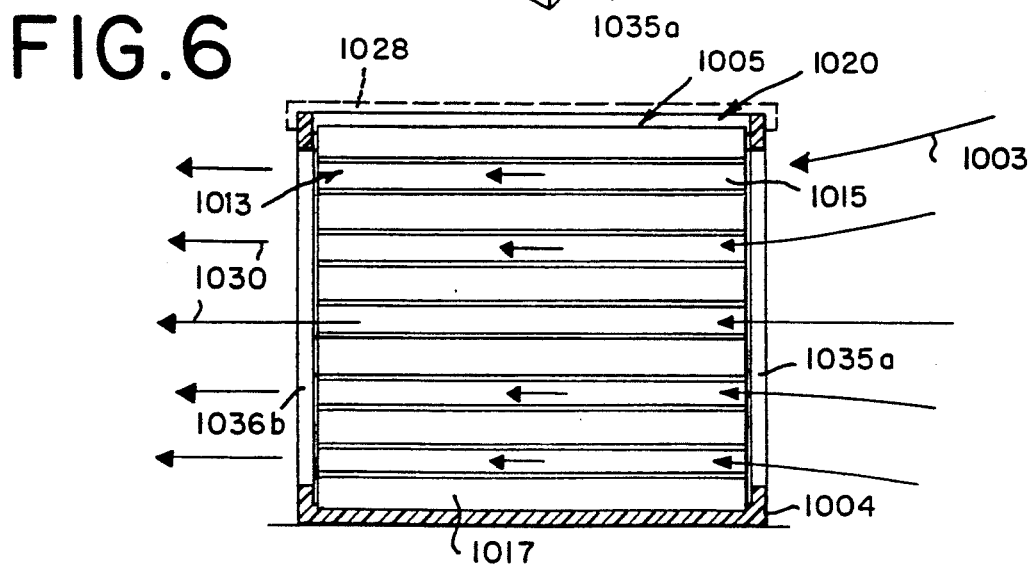
FIG. 6 is a cut-away elevation view of the apparatus of FIG. 5 along lines 6—6 of FIG. 5.

FIG. 6 is a cut-away side elevation view of the apparatus of FIG. 5 showing all of the articles 1005 in place and showing the use of lid 1028 to cover the top side of the apparatus as soon as the air 1003 to be freshened is commenced to be put into motion.

FIGS. 14 and 15 are perspective views of articles of my invention; similar to the articles of FIGS. 3 and 4 with the exception that instead of one circular void (36 in FIG. 3) and (46 in FIG. 4), the articles 500 of FIG. 14 and 600 of FIG. 15 have a multiplicity of circular voids perpendicular to the outer surfaces of the articles.

Thus referring to FIG. 14, FIG. 14 is a multi-layer sustained release tobacco flavor, scent, insect repellent, deodorant and/or air freshener-emitting rectangular-shaped article 500 consisting of:

(a) a sustained release scent, tobacco flavor, insect repellent, deodorant and/or air freshener-emitting susbstantially planar core lamina 52 consisting of a microporous or a macroporous polymer having included in the pores thereof a fragrance, insect repellent, and/or air freshener composition, (e.g., of porous vinyl halide-acrylated caprolactone such as that specifically disclosed in U.S. Pat. No. 4,950,693 issued on Aug. 21, 1990 the specification for which is incorporated by reference herein or a polyurethane as disclosed U.S. Pat. No. 4,950,694 or 4,950,542 issued on Aug. 21, 1990 the specifications for which are incorporated by reference herein (said core lamina 52 having a first upper planar surface $S_1$ of surface area $A_1$, a second lower planar surface $S_1'$ of surface area $A_1'$, a finite cross section thickness $d_1$ and a lateral exposed continuous or discretely interrupted surface area $S_e$ having an area $A_e$ being substantially in four linear lateral core planes immediately adjacent and perpendicular to one another, said lateral core planes being substantially perpendicular to said first upper planar surface and said second lower planar surface of said core lamina 52. As stated supra, the circular voids shown by reference numerals 56a, 56b, 56c and 56d cut through the article and travelling transversally from the upper surface of a barrier polymer lamina 50A coated onto the upper surface of the core polymer lamina 52 through the barrier layer and through the core polymer through a lower barrier polymer lamina 50b to the outer lower surface of said lower barrier lamina 50b;

(b) fixedly adhered to said first upper planar surface of said core lamina 52 an impermeable polymer first barrier lamina 50a which has a first upper surface of surface area $A_2$ and a second lower surface of surface area $A_3$, said second lower surface being fixedly contiguous with said first upper planar surface of said core lamina 52;

(c) fixedly adhered to said second lower planar surface $S_1'$ of said core lamina 52 a planar impermeable polymeric second barrier lamina 50b which has a third upper surface $S_4$ of surface area $A_4$ and a fourth lower surface $S_5$ of surface area $A_5$, said third upper surface $S_4$ being fixedly contiguous at 54a with said second lower planar surface $S_1'$. The core polymer lamina 52 is contiguous with the upper barrier polymer lamina 50a at 54b.

Referring to FIG. 15, FIG. 15 is a multi-layer sustained release tobacco flavor, scent, insect repellent, deodorant and/or air freshener emitting rectangular-shaped article 600 consisting of:

(a) a sustained release scent, tobacco flavor, insect repellent, deodorant and/or air freshener-emitting substantially planar core lamina 64 consisting of a microporous or macroporous polymer having included in the pores thereof a fragrance, insect repellent, deodorant, tobacco flavor and/or air freshener composition, said core lamina 64 having a first upper planar surface $S_1$ of surface area $A_1$, having an adhesive layer 62b coated thereon, a second lower planar surface $S_1'$ of surface area $A_1'$ having an adhesive layer 62a coated thereon, a finite cross section thickness $d_1$ and a lateral exposed discretely interrupted surface area $S_e$ having an area $A_e$ being substantially in four linear lateral core planes immediately adjacent and perpendicular to one another, said core planes being substantially perpendicular to said first upper planar surface and said second lower planar surface of said core lamina 64. Circular voids 66a, 66b, 66c and 66d are located transverse from uppper impermeable barrier 60a through core lamina 64 and through lower impermeable barrier polymer 60b thereby causing an additional exposed surface area to exist in article 100 at the center part of each of the circular (or "cylindrical") voids 66a, 66b, 66c and 66d;

(b) fixedly adhered via adhesive layer 62b to said first upper planar surface of said core lamina 64 a planar impermeable polymeric first barrier lamina 60a which has a first upper surface of surface area $A_2$ and a second lower surface of surface area $A_3$, said second lower surface being fixedly contiguous with the adhesive layer 62b covering said first upper planar surface of said core lamina 64;

(c) fixedly adhered via adhesive layer 62a to said second lower planar surface $S_1'$ of said core lamina 64, a planar impermeable polymeric second barrier lamina 60b which has a third upper surface $S_4$ of surface area $A_4$ and a fourth lower surface $S_5$ of surface area $A_5$, said third upper surface $S_4$ being fixedly contiguous (via adhesive layer 62a) with said lower planar surface $S_1'$.

Apparatus shown in FIGS. 16, 17, 18 and 20 is adaptable for the articles of FIGS. 14, 15, 3, 4 and 19.

The article of FIG. 19 is similar to the article of FIG. 7 with the exception that a circular or cylindrical void 1936 passes through the article from the outer surface 1917 thereof to the lower outer surface thereof.

Referring to FIG. 19, FIG. 19 is a multi-layer sustained release insect repellent, deodorant and/or air freshener-emitting rectangular-shaped article 1900 consisting of:

(a) a sustained release insect repellent, deodorant and/or air freshener-emitting substantially planar core lamina 1911 consisting of a microporous or macroporous polymer having included in the pores thereof an insect repellent, deodorant and/or air freshener composition, said core lamina 1911 having a first upper planar surface $S_1$ of surface area $A_1$ having separately-spaced n parallel-exposed rectangular areas $A_e''$ thereon 1915, a second lower planar surface $S_1'$ of surface area $A_1'$ having m separately spaced parallel exposed rectangular areas thereon 1915, a finite cross section thickness $d_1$ and a lateral exposed surface area $S_e'$ having an area $A_e'$ being substantially in linear lateral core planes immediately adjacent and perpendicular with one another, said lateral core planes being substantially perpendicular to said first upper planar surface and said second lower planar surface of said core lamina 1911;

(b) fixedly adhered to said first upper planar surface of said core lamina 1911 a series of n-spaced parallel-disposed first barrier laminae 1909a which has first upper surfaces 1917 of surface area $A_2$ and second lower surfaces of surface area $A_3$, said second lower surfaces each being fixedly contiguous with said first upper planar surface of said core lamina 1911; with the spaces between the parallel-disposed barrier laminae 1917 being indicated by reference numeral 1913; and the surface area of said spaces 1913 ($S_e''$) along surface $S_1$ being indicated by reference numeral 1915, (wherein);

$$A_e = A_e' + A_e''$$

(c) fixedly adhered to said second lower planar surface $S_1'$ of said core lamina 1911, a parallel-disposed series of m spaced second barrier laminae 1909b which has third upper surfaces $S_4$ of surface area $A_4$ and fourth lower surfaces $S_5$ of surface area $A_5$, said third upper surfaces $S_4$ being fixedly contiguous with said second lower planar surface $S_1'$. Adhesive layer 1919b adheres the parallel-disposed series of spaced barrier laminae 1909a and 1909b, at respectively, 1919a and 1919b. The cylindrical void 1936 passes through the lamina article 1900 from the outer surface of the parallel-disposed series of spaced barrier laminae 1917 through the adhesive layer 1919a, through the core lamina 1911, through the adhesive layer 1919b, and to the lower outer surface of the parallel-disposed series of spaced barrier laminae 1919b to the outer surface thereof (the lower surface thereof). The central part of the cylindrical void 1936 has an additional exposed lateral core lamina 1911 surface adapted for controlled release of insect repellent, air freshener and/or deodorant when utilized in conjunction with the apparatus of FIGS. 16, 17, 18 and 20.

Thus, referring to the apparatus of FIG. 16, the apparatus in its entirety is referred to by reference numeral 1600. Articles of the type set forth in FIGS. 14, 15 and 19 (shown by reference numeral 1400) are inserted into notches 1602 each of the articles has a center core lamina 1632, and outer impermeable barrier laminae 1630a and 1630b. Each of the articles has therethrough, transversally, cylindrical voids 1636. When not in use, the apparatus has removably adhered to the top thereof a peel-off tab 1640 covering a screen 1604. When in use, the peel-off tab 1640 is removed and air to be freshened or deodorized or insect repellent is passed through from intake 1650 through cylrindrical voids 1636 past the void 1608 through screen 1604 out the exhaust 1652 wherein the air now contains a small amount of insect repellent, air freshener and/or deodorant. The apparatus of FIG. 20 is similar to the apparatus of FIG. 16 with the exception that instead of the articles 1400 extending from notch 1602 completely across the apparatus to notch 1602, the articles are only located at an individual notch 2002 which, the necessity of, must have a greater depth than notches 1602 of apparatus 1600 of FIG. 16.

Thus, referring to the apparatus of FIG. 20, air to have imparted thereto deodorant, air freshener and/or insect repellent is taken in at location 2050 and travels past cylindrical voids 1636 through top hole 2008 of apparatus 2000 to the exhaust 2052. At exhaust 2052 the air now contains deodorant, air freshener and/or insect repellent. The articles are held in place at notches 2002.

Figure 17:
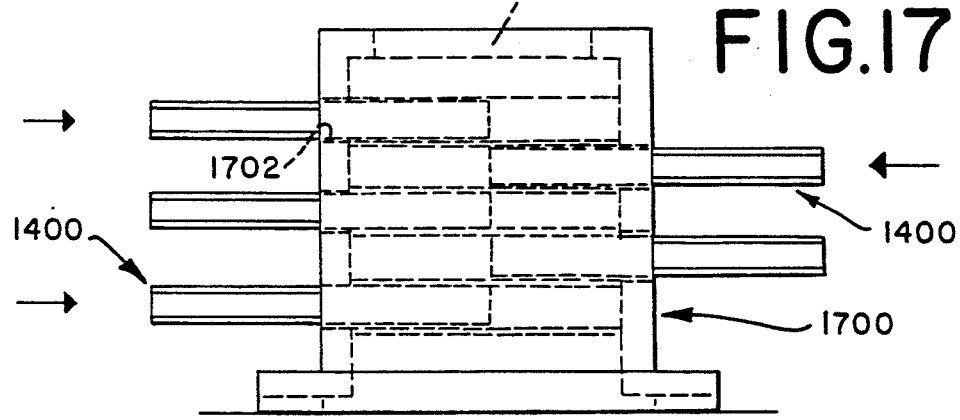
FIG. 17 and FIG. 18 sets forth cut-away side elevation views of another embodiment of the air freshener apparatus of my invention utilizing, inter alia, the articles as illustrated in FIG. 14.
Figure 18:
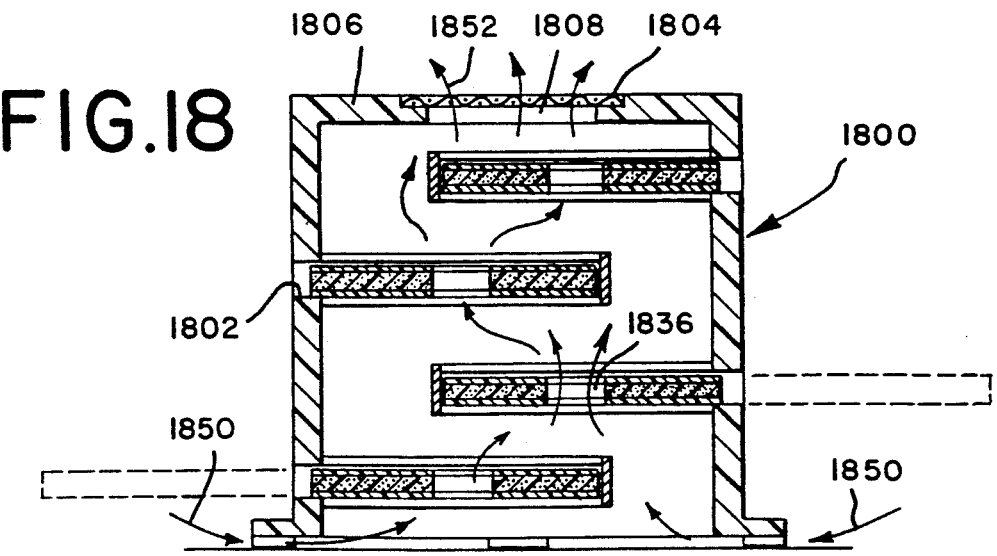

The apparatus of FIGS. 17 and 18 is similar to the apparatus of FIG. 20 with the exception that instead of using wedges, e.g., 1602 in FIG. 16, lateral loading openings 1802 are used to insert and support the articles of my invention having the cylindrical voids 1636. Thus, apparatus indicated by reference numeral 1800, when in operation has the articles of my invention inserted through openings 1802. Air at the intake 1850 passes through the circular or cylindrical voids 1936 through the opening of the apparatus 1808 to the exhaust 1852 where the air now contains deodorant, insect repellent and/or air freshener.

Figure 21:
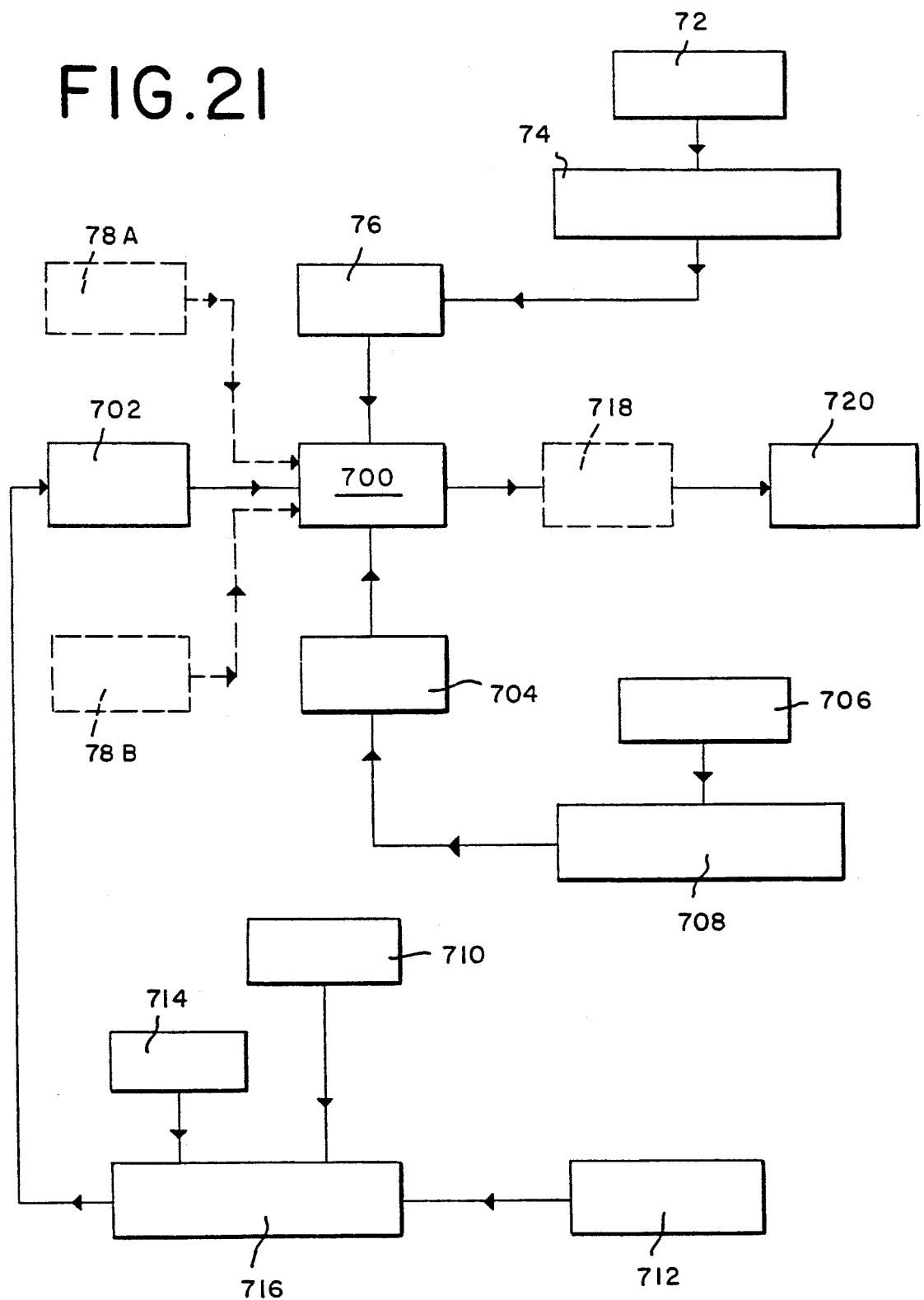
FIG. 21 is a schematic block flow diagram setting forth process steps and apparatus means for preparing articles of my invention such as that illustrated in FIG. 2.

FIG. 21 is a block flow diagram showing the process means and process steps for producing the articles of my invention adapted for insertion into the apparatus of my invention.

Polymer at location 72 is placed into a first extruder 74. The polymer at location 72 is of the impermeable type to be used, for example, in the creation of layer 10a of article 100 of FIG. 1. At the same time the core lamina is fabricated from polymer located at 712 which is placed into extruder 716 along with air freshener, insect repellent, perfume, deodorant and/or tobacco flavor. Thus from location 710 the organoleptic material or insect repellent or both are added to extruder 716. Simultaneously foaming material (optional) is added to extruder 716 from location 714. The extruder then forms the core polymer, e.g. indicated by reference numeral 12 of article 100 in FIG. 1 at location 702. Optionally, adhesive coatings from locations 78a and 78b are coated onto the core lamina coming from 702 at location 700. Over the adhesive layer (if present) are placed the nonpermeable or impermeable polymer laminar coatings, (e.g. 10a and 10b as shown in FIG. 1). Thus, impermeable polymer from location 706 is placed into extruder 708 where the impermeable coating at locations 704 is formed to be coated on the lower surface of the core polymer formed at location 702 (along with, and over, if desired, the adhesive from location 78b). The resulting article (e.g., 100 from FIG. 1 or 200 from FIG. 2) may then be pierced at location 718 in order to form the circular or cylindrical voids, e.g., 36 in FIG. 3 or 46 in FIG. 4 at location 718. The resulting product is then stored at location 720 for use, for example, in the air freshener, insect repellent and/or deodorant apparatus of, for example FIG. 5 or FIG. 16 or FIG. 17 or FIG. 18.

The coating apparatus for carrying out the coatings at such locations as location 700 in FIG. 7 is described in more detail with reference to the detailed description of FIGS. 22, 23, 24, 25, 26, 27, 28, 29, 30, 31, 32, 33, 34, and 35, infra.

The coating apparatus set forth in the diagrams in FIGS. 22-35, inclusive, is also described in the "Modern Plastics Encyclopedia, 1983-1984" published by McGraw-Hill Company at pages 195-200, inclusive.

Figure 22:
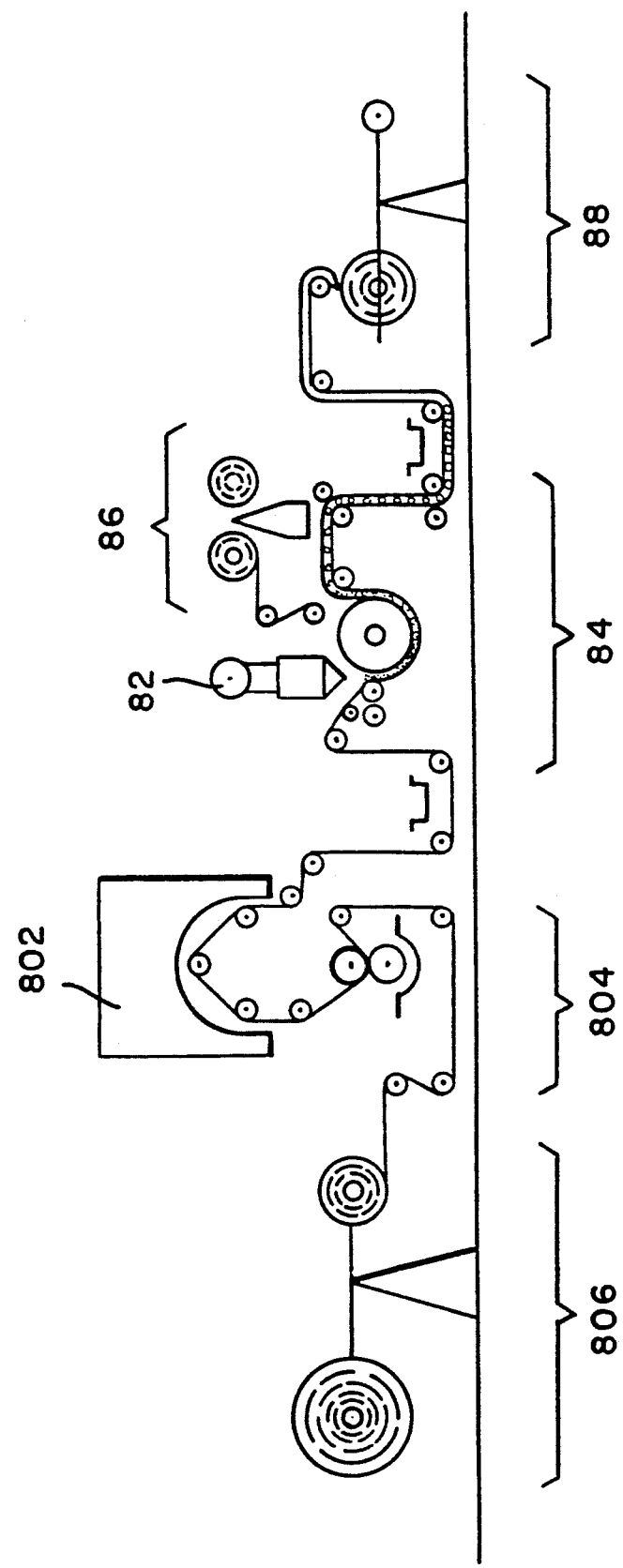
FIG. 22 is a schematic diagram of apparatus for extrusion coating and laminating whereby articles such as that illustrated in FIG. 1 can be produced.

Thus referring to FIG. 22, core layer from unwind section 806 is passed to primer section 804 and then to dryer section 802 simultaneously from auxiliary unwind section 86, impermeable layer (e.g., 10a in FIG. 1) is passed into extruder 82 with the layer from unwind section 806. The resulting laminate is then sent into section 88 where it is wound together. The same process can then be repeated in order to add the new impermeable layer (e.g., 10b of FIG. 1) to the laminate.

FIGS. 23-33b set forth various auxiliary apparatus for "roll coating" which apparatus is particularly adaptable to the creation of the articles of my invention.

FIG. 23 shows a roll coater using a single roll 94 to carry a web 96 below the surface of coating material 98 contained in a pan or reservoir 99 to yield coated material evolving from roller 92 and shown using reference numeral 91. Thus the web 96 would be the core polymer (shown by reference numeral 12, for example, in FIG. 1 for article 100) and the impermeable polymer material for laminae 10a and 10b in FIG. 1, for example, is as shown by reference numeral 98 in FIG. 23.

FIG. 24 shows a schematic diagram of a "Mayer Rod Coater." The apparatus of FIG. 24 shows the use of a roll 105 to supply an excess coating of, for example, impervious polymer from, for example, tank 107b to a web. The excess drawn into tank 107a (and shown as material by reference numeral 108) is removed by a small rod tightly wound with wire 101 shown in FIG. 24A (in detail). Rod 101 is rigidly supported to prevent deflection. The spaces between the wires govern the quantity remaining and since the surface of the core polymer has been completely wetted, the coating tends to flow and form a uniform film. The dry coating weight is controlled by changing the total solids or the wire sides. The coated roll passes roller 104 and the final web is shown using reference numeral 102.

FIG. 25 sets forth another variation of single roll coating, known as air knife coating utilizing a jet of air at 117 to remove excess material and smooth the wet film 113. Thus, web 114 (e.g., as core material) is coated with such material as impermeable polymer material 117 held in holding tank 118 and coated onto the web at 115 using roller 116. The thus coated web (with wet coating) is dried using jet 117 while the web passes around roller 112.

FIG. 26 shows a "kiss coating" apparatus wherein material 123 passing roller 122 is supplied to roller 120 at 124 wherein it is coated with (e.g., impermeable polymer lamina material) 128 which is coated from pervious-coated rolled 125 onto roll 120. Material adhering to the top roll 120 is wiped off by the web kissing it as it passes at location 124. More preferrably, the material at location 128 is adhesive which would form a precoating of adhesive onto the core polymer in fabricating an article such as that shown in FIG. 2 where the adhesive is shown at locations 22a and 22b coated onto core polymers lamina 24. Thus, for example, the coated web passing roller 121 would be preferrably core polymer 24 pre-coated with adhesive laminae 22a and 22b.

FIG. 27 set forths apparatus for carrying out a "squeeze-roll operation where web 132 passes roll 133 into a nip between rollers 130 and 134. Roller 134 picks up on its pervious layer coating material 136 (for both sides of web 132) and then evolves as coated web 131. Thus, impervious lamina forming material 136 (e.g., material to fabricate coatings 10a and 10b in article 100 of FIG. 1 is coated onto core lamina 12 (as web 132).

FIG. 28 sets forth a "gravure coating" apparatus which is a variation of two-roll coating in which metering is accomplished by cells engraved into a rolled surface. FIG. 28 shows direct gravure coating wherein coating 147 held in tank 146 is supplied to a rotating engraved roll 144 from a pan 146 filling the cells 145 and covering the roll surface. The excess is wiped off by a flexible doctor blade from 143. The coating remaining in the cells is transferred to the web 142 coming from roll 149 into nip 148 around roll 141 as the web passes through the nip. The web then goes round on the surface 140 of roll 141. The nip 148 between the rolls 141 and 144 may be controlled by mechanical stops or by pressure applied to the roll journals. The coating weight is determined by the volume of the cells, the total solids of the wet coating and the efficiency of transfer.

FIG. 29 shows gravure coating by means of "reverse gravure". In reverse gravure operation, the engraved roll 156 operates in the opposite direction to the web 151 and the nip between rolls 156 and 153 is maintained at very light contact by adjustable roll stops. The wiping action blends the dots together yielding uniform light coatings. Thus, web 151 is fed past roll 152 into nip 154 where it is coated from gravure roller 156 with coating held in tank 158; the coating being indicated by reference numeral 159. The web 151 passes around the surface of roller 153, the surface of roller 153 being indicated by reference numeral 150. The doctor blade wiping the gravure roll is indicated by reference numeral 155.

Offset gravure apparatus shown is FIG. 30 where a steel roll 162 is added and the web 160 passes through the upper nip 163. Webs can be run at high speeds while the engraved roll 166 operates at low speed without slinging coating 169 from the pan 168. Additionally, the transfer through two nips 1600 and 163 is used to split, smooth and attenuate the coating film for very fine high quality applications, for example, in the coating operations to form the articles of FIGS. 4 and 3. Thus, the web 160 passes roller 161 into nip 163 between rollers 162 and coating roller 165 having surface 164. The surface containing the coating 169 is applied from gravure roller 166 from the cells 1601 being wiped by doctor blade 167 after picking up the coating 169 from pan 168. The web 160 passes through nip 163 around roller 162 after which the web is dried to form an article which can be cut up to form articles such as that illustrated in FIGS. 1, 2, 3 and 4.

FIG. 31 shows a "reverse roll coating" operation wherein a premetered film of material 177 is transferred from a roll 174 turning in one direction to a web 170 on a roll 173 travelling in a reverse direction. All of the material (e.g., adhesive or impermeable polymer coating) 177 is transferred and no film splitting occurs. In its common form the gap between two precision ground chilled iron rolls 174 and 175 performs the metering operation. Thus web 170 passing roller 171 into nip 176 is coated at nip 176 provided by rollers 173 and 174. The web 170 passes around roller 173 on surface of roller 172 and the coated web is shown by using reference numeral 179.

FIG. 32 illustrates a nip-fed reverse roll coating apparatus. In this apparatus, the coating (e.g., impermeable layer or adhesive) is contained in a reservoir 180 formed by chilled iron rolls 182 and 187, a fountain plate 181 and two close fitting side dams. Coated width is controlled by the position of these side dams which can be in parallel thereby forming parallel-coated articles; that is, parallel coated wtih impermeable layer leaving wedges therebetween as is illustrated in FIG. 7, 10, 11, 11A, 12 and 13 described supra. This reverse roll coating operation is the most preferred of all of the coating methods, offering good weight control both across and down web regardless of web variations, good performance at high and low speeds and ability to handle a broad range of viscosities and coating materials. Thus, the web 183 is fed past roller 184 into nip 189 which is formed by roller 187 and roller 185. The web 183 proceeds around surface 186 through nip 189 to location 188 wherein it is already coated with the coating material held in resevoir 180.

FIGS. 33A and 33B illustrate apparatus used in Levelon (trademark of the Midland Ross Corporation) coating. Levelon coating utilizies precision chilled iron rolls (194 and 196 in FIG. 33A and 1900 and 1902 in FIG. 33B) to provide accurate metering as with reverse roll coaters. However, the web (190 in FIG. 33A and 1904 in 33B) is passed through the metering gap so that variations in web thickness are leveled. Extremely smooth coatings can be produced.

In FIG. 33A web 190 proceeds around roller 191 into nip 197 formed from rollers 194 and 196. Coating 192 formed from a reservoir held in place by dam 193 and side dams (not shown) is applied at nip 197 to web 190 whereupon web 190 is coated as shown by reference numeral 195.

In FIG. 33B web 1904 proceeds past roller 1905 and is coated by transfer roller 1908 which is partially immersed in coating 1906 which is held in reservoir 1907. The web proceeds through nip 1901 formed by rollers 1900 and 1902 and proceeds around roller 1902 wherein it is shown as coated web 1903.

Apparatus shown in FIGS. 34 and 35 sets forth apparatus carrying out the process of transfer coating.

Thus in FIG. 1 polyurethane is used in the transfer coating line. Roller 2001 is a release web unwind whereupon the web 2002 proceeds past accumulator rollers 2003 and past skin coat 2006 and then through the drying oven 2004; and then past cooling rolls 2020 around tie coat 2022 into the lamination rolling system 2005 whereupon the laminate is dried in drying oven 2006 and then the coated web now proceeds to the cooling roll 2007 and accumulator 2024 whereupon it proceeds into the rewind apparatus shown by rewind roll 2010; stripping roll 2009; and windup 2008 using roll 2011 as a rewind.

FIG. 21 shows the polyvinyl chloride transfer coating line with convection ovens. Release web unwind 2101 feeds web 2102 past roller 2103 into accumulator rolls 2104 and thence to skin coat 2126 into gel oven 2105. The web then proceeds past cooling rolls 2106 to a foam coat and thence into a gel oven; followed by lamination at rollers 2108; and then followed by a procession into an expanding oven 2109. The coated web then proceeds past cooling rolls 2130 and accumulator 2110 to the rewind/stripping/windup apparatus with windup roll 2112; stripping roll 2114 and rewind rolls 2120 and 2121. The stripping process involves the use of two rolls, one of which is used to store the finished product and the other to store release web for reuse. Before proceeding to windup and stripping rolls 2114 and 2112 the webs 2116A and 2116B pass through rolls 2118A and 2118B.

FIGS. 36, 37, 37A, 37B and 38 show steps in creating small articles useful, for example, in a potpourri, with the articles fabricated from such larger articles as illustrated in FIG. 1.

Referring to FIG. 36, core lamina 2204 having coatings thereon of impermeable polymer 2201A and 2201B adhered to the core lamina 2204 are marked with appropriate designs, 2300A and 2300B. The smaller articles having ornamental designs are cut or punched out of the article and shown in FIGS. 37A and 37B as articles 2306a and 2306b, respectively.

Thus in FIG. 37A, an ornamental design of a "spade", a playing card symbol is a central core lamina 2304a and an impermeable surface on either surface of the core lamina 2304a. The upper surface being impermeable and indicated by reference numeral 2301a and the lower surface being impermeable and indicated by reference numeral 2301b. The outer surface of the article 2300a is indicated by reference numeral 2306a.

Referring to FIG. 37B, a triangular-shaped small article useful in the potpourri of FIG. 38 is formed by punching out the article from the larger article of FIG. 36. The article of FIG. 37B has a central core section 2304c and on the outer surfaces thereof; on the upper surface impermeable polymeric lamina 2301c having an outer surface 2306b and a lower impermeable polymeric lamina 2301d. The article itself is indicated by reference numeral 2300b.

Articles such as 2300a and 2300b are incorporated into the transparent container of FIG. 38 and shown by reference numeral 2400a and 2400b. The container is indicated by reference numeral 2403 and its base is indicated by reference numeral 2404. The container of FIG. 38 is shown as a transparent container.

FIG. 39 illustrates a multi-layered sustained release tobacco flavor, scent, insect repellent, deodorant and/or air freshener emitting lamina article comprising:

(a) a sustained release scent, tobacco flavor, insect repellent, deodorant and/or air freshener emitting substantially planar core lamina 3903 consisting of a microporous or macroporous polymer having included in the pores thereof a fragrance, tobacco flavor, insect repellent, deodorant and/or air freshener composition, said core lamina having a first upper planar surface $S_1$ of surface area $A_1$, a second lower planar surface $S_1'$ of surface area $A_1'$, a substantially uniform finite cross section thickness $d_1$ and a lateral discretely interrupted rectangular-shaped surface area $S_e$ having an area $A_e$ being substantially in linear lateral core planes immediately adjacent or conterminous to and juxtaposed to one another, said lateral core plane or core planes being substantially perpendicular to said first upper planar surface and said second lower planar surface of said core lamina;

(b) fixedly adhered to said first upper planar surface of said core lamina 3903 and contiguous (or coplanar) therewith an impermeable polymeric first barrier lamina 3902a which has a first upper surface $S_2$ of surface area $A_2$ and a second lower surface $S_3$ of surface area $A_3$, said second lower surface being fixedly contiguous (or coplanar) with said first upper planar surface of said core lamina 3903;

(c) fixedly adhered to said second lower planar surface $S_1'$ of said core lamina 3903 and contiguous (or coplanar) therewith at least one planar impermeable polymeric second barrier lamina 3902b which has a first upper surface $S_4$ of surface area $A_4$ and a second lower surface $S_5$ of surface area $A_5$, said first upper surface $S_4$ being fixedly contiguous (or coplanar) with said second lower planar surface $S_1$ of the core lamina 3903;

(d) fixedly adhered to said first upper surface $S_2$ of said first barrier lamina 3902a (and contiguous or coplanar therewith) a porous or macroporous "Burst" immediate release scent, tobacco flavor, insect repellent, deodorant and/or air freshener-emitting substantially planar first "Burst" lamina 3901a consisting of a microporous or macroporous polymer having included in the pores thereof a fragrance, tobacco flavor, insect repellent, deodorant and/or air freshener composition, said first "Burst" lamina 3901a having a first upper outer exposed surface (that is exposed to the environment surrounding the article) $S_6$ of surface area $A_6$ and a second lower inner surface $S_7$ of surface area $A_7$, said surface $S_7$ being fixedly contiguous (or coplanar) with said first upper surface $S_2$ of said first barrier lamina 3902a;

(e) fixedly adhered to said second lower surface $S_5$ of said second barrier lamina 3902b, and contiguous or coplanar therewith, a porous or microporous scent, tobacco flavor, insect repellent, deodorant and/or air freshener-emitting substantially planar second "Burst" lamina 3901b consisting of a microporous or macroporous polymer having included in the pores thereof a fragrance, tobacco flavor, insect repellent, deodorant and/or air freshener composition, said second "Burst" lamina 3901b having a first lower outer exposed surface (that is exposed to the environment surrounding the article) $S_8$ of surface area $A_8$ and a second upper inner surface $S_9$ of surface area $A_9$ said surface $S_9$ being fixedly contiguous (or coplanar) with said surface $S_5$.

Figure 40:
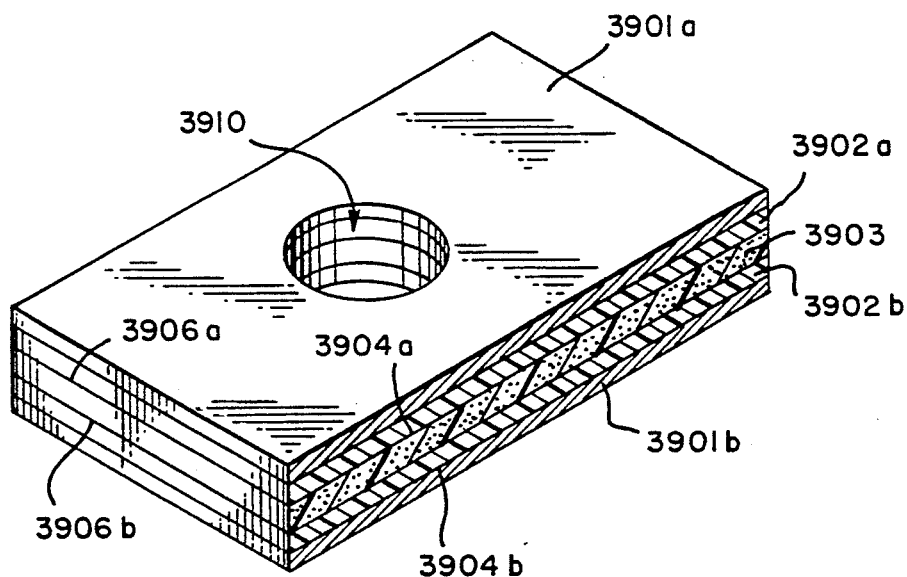
FIG. 40 is another embodiment of the article as illustrated in FIG. 39, specially adapted to be used in such apparatus as that illustrated in FIG. 20.

FIG. 40 in an article similar to FIG. 39 with the exception that transverse from the outer upper surface of the "Burst" polymer lamina through the article to the lower "Burst" polymer layer is a cylindrical void 3910, the sides of which are parallel to the linear lateral core plane of the core lamina.

What is claimed is:

1. A multi-layer controlled release functional organoleptic material-emitting lamina article comprising:

(a) a controlled release functional organoleptic material-emitting substantially planar core lamina consisting of a microporous or macroporous polymer having included in the pores thereof a functional organoleptic material composition, said core lamina having a first upper planar surface $S_1$ of surface area $A_1$, a second lower planar surface, $S_1'$, of surface area $A_1'$, a substantially uniform finite cross section thickness $d_1$ and a lateral continuous or discretely interrupted surface area $S_e$ having an area $A_e$ which surface area $A_e$ is exposed to the environment surrounding the article, being substantially in linear lateral core planes, immediately adjacent or conterminous to and juxtaposed to one another or in a curvilinear lateral core plane or in curvilinear lateral core planes immediately adjacent or conterminous to and juxtaposd to one another, said lateral core plane or core planes being substantially perpendicular to said first upper planar surface and said second lower planar surface of said core lamina wherein:

$$A_1 = A_1' >>> A_e$$

and;

$$S_e \perp (S_1 \wedge S_1')$$

(b) fixedly adhered to said first upper planar surface of said core lamina and contiguous or coplanar therewith at least one planar impermeable polymeric first barrier lamina or series of monoplanar spaced parallel first barrier laminae which has a first upper surface $S_2$ of surface area $A_2$ and a second lower surface $S_3$ of surface area $A_3$, said second lower surface being fixedly contiguous or coplanar with said first upper planar surface of said core lamina with the provisos that:

$$A_1 = A_1' \geq A_3 \geq A_2$$

and;

$$S_1 \parallel S_1' \parallel S_3 \parallel S_2$$

(c) fixedly adhered to said lower planar surface $S_1'$ of said core lamina and contiguous or coplanar therewith at least one planar impermeable polymeric second barrier lamina or a series of spaced parallel second barrier laminae which has a first upper surface $S_4$ or surface area $A_4$ and a second lower surface $S_5$ of surface area $A_5$, said first upper surface $S_4$ being fixedly contiguous or coplanar with said second lower planar surface $S_1$ of the core lamina with the provisos that:

$$A_1' \geq A_4 \geq A_5$$

and;

$$S_1' \parallel S_4 \parallel S_5.$$

2. A multi-layer controlled release functional organoleptic material-emitting article consisting of:

(a) a controlled release functional organoleptic material-emitting substantially planar core lamina consisting of a microporous or a macroporous polymer having included in the pores thereof a functional organoleptic material composition, said core lamina having a first upper planar surface $S_1$ of surface area $A_1$, having an adhesive layer coated thereon, a second lower planar surface, $S_1'$ of surface area $A_1'$ having an adhesive layer coated thereon, a finite cross section thickness $d_1$ and a lateral exposed continuous or discretely interrupted surface area $S_e$ having an area $A_e$ being substantially in linear lateral core planes immediately adjacent or conterminous to and juxtaposed to one another or in a curvilinear lateral core plane or in curvilinear lateral core planes immediately adjacent or conterminous to and juxtaposed to one another, said lateral core plane or core planes being substantially perpendicular to said first upper planar surface and said second lower planar surface of said core lamina; wherein:

$$A_1 = A_1' >>> A_e;$$

(b) fixedly adhered via the adhesive layer, to said first upper planar surface of said core lamina a planar impermeable polymeric first barrier lamina or series of monoplanar spaced parallel first barrier laminae which has a first upper surface $S_2$ of surface area $A_2$ and a second lower surface $S_3$ of surface area $A_3$, said second lower surface being fixedly contiguous or coplanar with the adhesive layer covering said first upper planar surface of said core lamina with the provisos that:

$$A_1 = A_1' \geq A_3 \geq A_2$$

and;

$$S_1 \parallel S_1' \parallel S_3 \parallel S_2$$

(c) fixedly adhered via an adhesive layer to said second lower planar surface $S_1'$ of said core lamina a planar impermeable polymeric first barrier lamina or series of monoplanar spaced parallel first barrier laminae which has a first upper surface $S_2$ of surface area $A_2$ and a second lower surface $S_3$ of surface area $A_3$, said second lower surface being fixedly contiguous or coplanar with the adhesive layer covering said first upper planar surface of said core lamina with the proviso that:

$$A_1 = A_1' >>> A_e$$

and;

$$S_1' \parallel S_4 \parallel S_5.$$

3. A multi-layer controlled release functional organoleptic material-emitting lamina article comprising:

(a) a functional organoleptic material-emitting substantially planar core lamina consisting of a microporous or a macroporous polymer having included in the pores thereof a functional organoleptic material composition, said core lamina having a first upper planar surface $S_1$ of surface area $A_1$, a second lower planar surface, $S_1'$ of surface area $A_1'$, a substantially uniform finite cross section thickness $d_1$ and a lateral continuous or discretely interrupted surface area $S_e$ having an area $A_e$ which surface area $A_e$ is exposed to the environment surrounding the article, being substantially in linear lateral core planes immediately adjacent or conterminous to and juxtaposed to one another or in a curvilinear lateral core plane or in curvilinear lateral core planes immediately adjacent or conterminous to and juxtaposed to one another, said lateral core plane or core planes being substantially perpendicular to said first upper planar surface and said second lower planar surface of said core lamina wherein:

$$A_1 = A_1' >>> A_e$$

and;

$$S_e \perp (S_1 \wedge S_1')$$

(b) fixedly adhered to said first upper planar surface of said core lamina and contiguous or coplanar therewith at least one planar impermeable polymeric first barrier lamina or series of monoplanar spaced parallel first barrier laminae which has a first upper surface $S_2$ of surface area $A_2$ and a second lower surface $S_3$ of surface area $A_3$, said second lower surface being fixedly contiguous or coplanar with said first upper planar surface of said core lamina with the provisos that:

$$A_1 = A_1' \geq A_3 \geq A_2$$

and;

$$S_1 \parallel S_1' \parallel S_3 \parallel S_2$$

(c) fixedly adhered to said lower planar surface $S_1'$ of said core lamina and contiguous or coplanar therewith at least one planar impermeable polymeric second barrier lamina or a series of spaced parallel second barrier laminae which has a first upper surface $S_4$ of surface area $A_4$ and a second lower surface $S_5$ of surface area $A_5$, said first upper surface $S_4$ being fixedly contiguous or coplanar with said second lower planar surface $S_1$ of the core lamina with the provisos that:

$$A_1' \geq A_4 \geq A_5$$

and;

$$S_1' \parallel S_4 \parallel S_5$$

(d) fixedly adhered to said first upper surface $S_2$ of said first barrier lamina and contiguous or coplanar therewith a porous or microporous "Burst" immediate release functional organoleptic material-emitting substantially planar first "Burst" lamina or series of monoplanar spaced parallel first "Burst" laminae consisting of a microporous or a macroporous polymer having included in the porous thereof a functional organoleptic material composition, said first "Burst" lamina having a first upper outer exposed surface, exposed to the environment surrounding the article, $S_6$ of surface area $A_6$ and a second lower inner surface $S_7$ of surface area $A_7$, said surface $S_7$ being fixedly contiguous or coplanar with said first upper surface $S_2$ of said first barrier lamina with the provisos that:

$A_2 \geqq A_7$ and $S_2 \| S_7$;

(e) fixedly adhered to said second lower surface $S_5$ of said second barrier lamina and contiguous or coplanar therewith a porous or microporous functional organoleptic material-emitting substantially planar second "Burst" lamina or series of monoplanar spaced parallel second "Burst" laminae consisting of a microporous or a macroporous polymer having included in the pores thereof a functional organoleptic material composition, said second "Burst" lamina having a first lower outer exposed surface, exposed to the environment surrounding the article, $S_8$ of surface area $A_8$ and a second upper inner surface $S_9$ of surface area $A_9$, said surface $S_9$ being fixedly contiguous or coplanar with said surface $S_5$ with the provisos that:

$A_5 \geqq A_9$ and $S_5 \| S_9$.

4. The article of claim 1 having a cylindrical void thereto parallel to the said lateral linear core plane or planes and extending from the upper outer surface $S_2$ of the impermeable polymeric first barrier lamina to the lower outer surface $S_5$ of the planar impermeable polymeric second barrier lamina.

5. The article of claim 1 having therethrough a plurality of cylindrical voids the size of which are parallel to each of the lateral core planes, each of which void extends from the upper outer surface $S_2$ of the impermeable polymeric first barrier lamina to the lower outer surface $S_5$ of the impermeable polymeric second barrier lamina.

6. A multi-layer controlled release functional organoleptic material-emitting rectangular shaped article consisting of:
(a) a controlled release functional organoleptic material-emitting substantially planar core lamina having a finite cross section thickness $d_1$ consisting of a microporous or a macroporous polymer having included in the pores thereof a functional organoleptic material composition, said core lamina having a first upper planar surface $S_1$ of surface area $A_1$, having n separately spaced parallel exposed rectangular surfaces $S_e''$ having a surface area $A_e''$ thereon which are a first set of lateral core planes parallel and adjacent to one another, a second lower planar surface $S_1'$ having surface area $A_1'$ having m separately spaced parallel exposed rectangular surfaces $S_e'$ having surface area $A_e'$ thereon which are a second set of lateral core planes parallel and adjacent to one another, said lateral core planes being substantially parallel to said first upper planar surface and said second lower planar surface of said core lamina, with the total exposed core lamina surface $S_e$ having area $A_e$ wherein:

$A_1 = A_1' >>> A_e$ and $S_e \| (S_1 \wedge S_1')$ (b) fixedly adhered to said first upper planar surface of said core lamina a series of n spaced parallel-disposed monoplanar first barrier laminae which have first upper surfaces of surface area $A_2$ and second lower surfaces of surface area $A_3$, said second lower surfaces each being fixedly contiguous with said first upper planar surface of said core lamina with the provisos that:

$A_e = A_e' + A_e''$;

$A_1 = A_1' \geqq A_3 \geqq A_2$ and $S_1 \| S_1' \| S_3 \| S_2$.

(c) fixedly adhered to said second lower planar surface $S_1'$ of said core lamina a parallel-disposed series of m spaced around barrier lamina which have third upper surfaces $S_4$ of surface area $A_4$ in fourth lower surfaces $S_5$ of surface area $A_5$, said third upper surfaces $S_4$ being fixedly contiguous with said second lower planar surface $S_1'$ with the provisos that:

$A_1' \geqq A_4 \geqq A_5$ and $S_1' \| S_4 \| S_5$.

7. Apparatus in the shape of a rectangular paralalelepiped for effecting controlled release of functional organoleptic materials, comprising an upright frame having two pairs of opposite vertically disposed sides; a first pair of sides and a second pair of sides and an upper planar top covering in a plane perpendicular to each of said first pair of sides and said second pair of sides, the first pair of sides having means for supporting a substantially horizontal planar disposition, perpendicular to the plane of the first pair of sides and the second pair of sides, and parallel to said upper planar top covering, one or a plurality of articles defined according to claim 4; with at least one of the articles of claim 4 being supported by said means, at least one entry portal permitting ingress of air to be treated, located in a side of said first pair of said second pair at a level below the location of the lower outer surface $S_5$ of the planar impermeable polymeric second barrier lamina of the lower-most supporting article of claim 4; and a second exit portal permitting egress of treated air at a location in the upper planar top covering and/or in a side of first pair or said second pair at a level above the location of the upper outer surface $S_2$ of the planar impermeable polymeric first barrier lamina of the uppermost article of claim 4; and means to force air to be treated through the first entry portal.

8. Apparatus in the shape of a rectangular parallelepiped for effecting controlled release of functional organoleptic materials comprising an upright frame having two pairs of opposite vertically disposed sides; a first pair of sides and a second pair of sides and an upper planar top covering in a plane perpendicular to each of said first pair of sides and said second pair of sides, the first pair of sides having means for supporting in a substantially horizontal planar disposition, perpendicular to the plane of the first pair of sides and the second pair of sides and parallel to said upper planar top covering, one or a plurality of articles defined according to claim 5 with at least one of the articles of claim 5 being supported by said means; at least one entry portal permitting ingress of air to be treated located in a side of said first said pair or said second pair at a level below the location of the lower outer surface $S_5$ of the planar impermeable polymeric second barrier lamina of the lower-most supported article of claim 5; and a second exit portal permitting egress of treated air at a location in the upper planar top covering and/or in a side of said first pair of said second pair at a level above the location of the upper outer surface $S_2$ of the planar impermeable polymeric first barrier lamina of the uppermost article of claim 5; and means to force air to be treated through the first entry portal.

9. Apparatus in the shape of a rectangular parallelepiped for effecting controlled release of functional organoleptic materials comprising an upright frame having two pairs of opposite vertically disposed sides; a first pair of sides and a second pair of sides; the first pair of sides having a first entry portal permitting ingress of air to be treated and a second exit portal permitting egress of treated air; means to force air to be treated through the first entry portal; the second pair of sides being substantially impermeable to fluids; and a rectangular top containing a plurality of rectangular slot openings parallel to one another; and parallel to said second pair of sides; and perpendicular to said first pair of sides; each of said slot openings being of such measurements and the vertical dimension of the frame being such that the slot openings permit entry in a close fitting manner and in the entirety of the article of claim 6; containing the articles of claim 6 whereby the parallel disposed series of spaced barrier laminae of said articles of claim 6 are in planes parallel to said second pair of sides and are perpendicular to said first pair of sides, thereby causing air to be treated to have direct contact with the parallel exposed rectangular area $A_e''$ of the core lamina of the article of claim 6.

* * * * *